(12) United States Patent
Shea

(10) Patent No.: US 6,638,198 B1
(45) Date of Patent: *Oct. 28, 2003

(54) EXERCISE SYSTEM

(76) Inventor: Michael J. Shea, 1726 Creek Crossing Rd., Vienna, VA (US) 22182

( * ) Notice: Subject to any disclaimer, the term of this patent is extended or adjusted under 35 U.S.C. 154(b) by 0 days.

This patent is subject to a terminal disclaimer.

(21) Appl. No.: 09/440,097

(22) Filed: Nov. 15, 1999

Related U.S. Application Data

(63) Continuation of application No. 08/842,113, filed on Apr. 28, 1997, now Pat. No. 6,050,924.

(51) Int. Cl.[7] ............................................. A63B 21/00
(52) U.S. Cl. ......................... 482/8; 484/4; 484/901
(58) Field of Search ............................. 482/51, 52, 53, 482/57, 1–9, 900, 901, 902

(56) References Cited

U.S. PATENT DOCUMENTS

| | | |
|---|---|---|
| 3,767,195 A | 10/1973 | Dimick |
| 4,112,928 A | 9/1978 | Putsch |
| 4,358,105 A | 11/1982 | Sweeney, Jr. |
| 4,571,682 A | 2/1986 | Silverman et al. |
| 4,642,769 A | 2/1987 | Petrofsky |
| 4,708,337 A | 11/1987 | Shyu ........................ 482/54 |
| 4,828,257 A | 5/1989 | Dyer et al. |
| 4,842,274 A | 6/1989 | Oosthuizen et al. |
| 4,907,795 A | 3/1990 | Shaw et al. ................ 482/9 |
| 4,934,694 A | 6/1990 | McIntosh .................. 482/9 |
| 5,020,795 A | 6/1991 | Airy et al. |
| 5,067,710 A | 11/1991 | Watterson et al. ............ 482/9 |
| 5,142,358 A | 8/1992 | Jason ..................... 434/247 |
| 5,207,621 A | 5/1993 | Koch et al. .................. 482/53 |
| 5,213,555 A | 5/1993 | Hood et al. |
| 5,246,411 A | 9/1993 | Rackman .................... 482/57 |
| 5,361,091 A | 11/1994 | Hoarty et al. ................. 348/7 |
| 5,374,227 A | 12/1994 | Webb ...................... 482/52 |
| 5,387,164 A | 2/1995 | Brown, Jr. |
| 5,410,472 A | 4/1995 | Anderson .................... 482/9 |
| 5,462,504 A | 10/1995 | Trulaske et al. |
| 5,512,025 A | 4/1996 | Dalebout et al. ........... 482/903 |
| 5,516,334 A | 5/1996 | Easton ....................... 482/8 |
| 5,547,439 A | 8/1996 | Rawls et al. |
| 5,553,860 A | 9/1996 | Zelikovich ................. 273/371 |
| 5,591,104 A | 1/1997 | Andrus et al. |
| 5,655,997 A | 8/1997 | Greenberg et al. ............. 482/5 |
| 5,706,822 A | 1/1998 | Khavari .................... 600/483 |
| 5,785,630 A | 7/1998 | Bobick et al. |
| 5,810,747 A | 9/1998 | Brudny et al. |
| 5,890,997 A | 4/1999 | Roth ......................... 482/8 |
| 5,916,063 A | 6/1999 | Alessandri ................... 482/4 |
| 5,931,763 A | 8/1999 | Alessandri ................... 482/4 |
| 5,944,633 A | 8/1999 | Wittrock .................... 482/4 |
| 5,947,869 A | 9/1999 | Shea ........................ 482/8 |
| 5,949,951 A | 9/1999 | Sklar et al. ................. 386/46 |
| 5,961,332 A | 10/1999 | Joao ...................... 434/236 |
| 6,042,519 A | 3/2000 | Shea ....................... 482/57 |
| 6,050,924 A | 4/2000 | Shea ....................... 482/57 |
| 6,059,692 A | 5/2000 | Hickman .................... 482/8 |
| 6,171,218 B1 | 1/2001 | Shea ....................... 482/57 |

*Primary Examiner*—Stephen R. Crow

(57) ABSTRACT

An exercise system includes a plurality of exercise terminals, wherein a workout of an exerciser includes at least two exercises performed at one or more of the exercise terminals. Each exercise terminal includes a communication device for communicating to the exerciser information regarding an exercise of the workout subsequent to a current exercise in the workout.

41 Claims, 16 Drawing Sheets

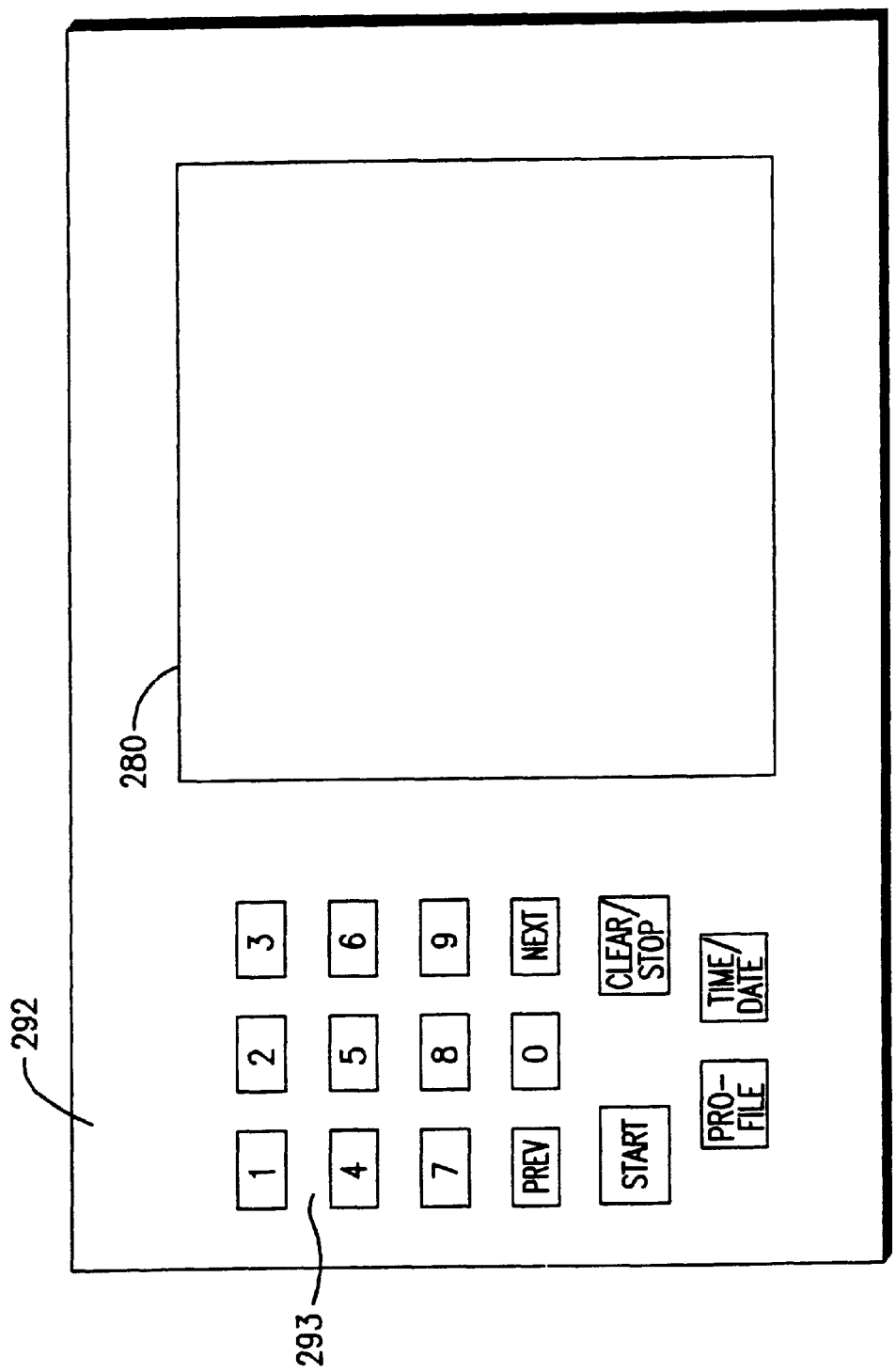

| EXERCISE IDENTIFIER |
|---|
| NAME |
| POSTAL ADDRESS |
| TELEPHONE NUMBERS(S) |
| E-MAIL ADDRESS |
| MESSAGES |
| PROFILE DATA |
| FUTURE EXERCISE DATA |
| PREVIOUS EXERCISE DATA |

FIG. 11A

| EXERCISE TERMINAL IDENTIFIER |
|---|
| EXERCISE TERMINAL TYPE DATA |
| PURCHASE DATA |
| USE DATA |
| LOCATION DATA |
| MAINTENANCE DATA |
| MANUFACTURER DATA |

FIG. 11B

| EXERCISE IDENTIFIER |
|---|
| EXERCISE TYPE IDENTIFIER |
| EXERCISE DESCRIPTION |
| PROFILE DATA |
| PARAMETERS |

FIG. 11C

| EXERCISE IDENTIFIER |
|---|
| EXERCISE TERMINAL TYPE IDENTIFIER |

FIG. 11D

|  | STRETCHING | STATIONARY BICYCLE | STEPPER |
|---|---|---|---|
| SEQ. NO. | 1-1 | 1-2 | 1-3 |
| EXERCISE ID | 01 | 02 | 03 |
| TERM. TYPE ID | 01 | 02 | 07 |
| PARAMETERS | 5:00 min. | 12:00 min. | 8:00 min. |
|  |  | Level 8 | Level 9 |

FIG. 12

EXERCISE SYSTEM

This application is a continuation of application Ser. No. 08/842,113, filed Apr. 28, 1997, now U.S. Pat. No. 6,050,924.

BACKGROUND OF THE INVENTION

1. Technical Field

The present invention generally relates to an exercise system and, more particularly, to an exercise terminal network including exercise terminals usable by an exerciser in a training or rehabilitation program. The exercise terminal network facilitates the use of different exercise terminals by an exerciser during a workout.

2. Description of Related Art

An exerciser participating in a training or rehabilitation program will generally perform a variety of exercise activities. These activities can include stretching, walking, biking, swimming, and jogging, as well as the utilization of one or more exercise devices. Such exercise devices include, for example, weight machines, stair climbers, steppers, rowing machines, ski machines, treadmills, cross trainers, and stationary bicycles. Some of these devices are part of exercise apparatus or machines and are controllable by controllers (such as processors) in accordance with exerciser-selected program data which sets and/or varies the exercise level. FIGS. 1 and 2 illustrate a stationary bicycle 5 which provides automatically-varying exercise levels as disclosed in U.S. Pat. No. 4,358,105 to Sweeney, Jr. The control system for the stationary bicycle includes a microcomputer which communicates electronically with a keyboard 12, a read-only memory 14, and a display 16. The read-only memory 14 stores the operating program for microcomputer 10 and a plurality of pre-stored exercise programs which are selectable by an exerciser. Movement of pedals 20 rotates a sprocket 22, which causes a chain 24 to drive a small diameter sprocket 26 attached to a flywheel 28. The variable load which an exerciser must overcome in order to rotate sprocket 22 is generated by an alternator 30, which provides a variable resistance to the effort of the exerciser through its driving connection with flywheel 28 by a gear belt 32. Microcomputer 10 controls the loading circuit of alternator 30. The output of microcomputer 10 on line 34 is a pulse width modulated signal, the width of which is proportional to the effort required by the exerciser. The changes in pulse width vary the field current in the alternator to cause variations in the resistance of the alternator to the force exerted by the operator. An exerciser using the stationary bicycle may select a pre-stored exercise program from read-only memory 14 for execution by microcomputer 10 to automatically vary the exercise difficulty level by generating pulses whose width is a function of the effort required by the exerciser. Using keyboard 12, an exerciser is also able to select a difficulty level and an exercise time.

Other exercise apparatus are shown in U.S. Pat. No. 4,708,337 to Shyu; U.S. Pat. No. 4,828,257 to Dyer et al.; U.S. Pat. No. 5,067,710 to Watterson et al.; U.S. Pat. No. 5,462,504 to Trulaske et al.; and U.S. Pat. No. 5,512,025 to Dalebout et al.

From workout to workout, an exerciser will often vary his/her exercise activities to achieve particular fitness goals and/or to avoid injury. For example, the exerciser may vary the time, the distance and/or the speed of his/her jogging from workout to workout. Similarly, the exerciser may vary the exercise apparatus used, as well as the exercise program, the different difficulty level(s) and/or the total exercise time from workout to workout. Thus, for example, an exerciser using an exercise apparatus may select exercise program data (for example, an exercise program a difficulty level, and/or a total exercise time) which defines a relatively easy workout on a day following a relatively hard workout. Or, an exerciser may utilize a stationary bicycle and a stair climber during one workout and a treadmill and weight machines during another workout. In addition, after several months of a training routine, an exerciser will likely find that he/she is able to perform at higher activity levels. In the case of jogging, this may mean the exerciser is able to jog for longer times and distances at higher speeds. In the case of using an exercise apparatus, it may mean that the exerciser is able to use the exercise apparatus at higher difficulty levels and/or for longer total exercise times.

However, exercisers attempting to achieve specific fitness goals may have problems selecting exercises, exercise apparatus, and/or exercise program data for each of the exercise apparatus to best achieve their goals and to maximize the benefits of workouts. While health clubs may have fitness consultants who assist exercisers in the initial selection of exercise apparatus, exercise program data, and other exercises which are best suited for the exerciser and his/her fitness goals, exercisers are often left on their own after this initial assistance. As the exerciser's fitness level increases, the initial selections of exercise apparatus, exercise program data, and other exercises may no longer be suitable. While an exerciser could hire a fitness consultant, this can be very expensive for exercisers participating in a long-term training program.

Additionally, exercisers who use, exercise apparatus at home and exercise on their own generally do not have fitness consultants available to guide them through the selection of particular exercise apparatus, exercise program data, and other exercises to achieve specific exercise goals. Such guidance may be particularly important for persons following a program of exercise prescribed by a doctor. For example, the Agency for Health Care Policy and Research recently recommended that rehabilitation programs for heart attack patients include exercise training customized to fit the patient's heart condition and other physical traits. While patients could undertake such rehabilitation programs on their own, a panel of cardiologists gathered by the Agency reported that studies have shown that patients who participate in comprehensive rehabilitation programs under close physician scrutiny are more likely to follow better heart habits for life, while those who try on their own often fail. Particularly important is a customized exercise program, where a doctor determines which exercises (e.g., walking or bicycling) are best, as well as how much exertion the patient can take. Where such rehabilitation programs utilize exercise apparatus such as treadmills, stationary bicycles, stair climbers, and the like, the exercise program data selected by the patient must be carefully chosen in view of the particular patient's recovery and physical characteristics. Participation in other exercises such as jogging or biking must also be based on the patient's recovery and physical characteristics. The selection of exercise apparatus, of exercise program data, and of other exercises may be difficult for the patient.

For these and other reasons, exercisers frequently do not receive the full benefits of their exercise because the selected exercise program data or other exercises are either too easy or too difficult or not well-suited to the ultimate fitness/medical goals or medical history of the exerciser.

SUMMARY OF THE INVENTION

One or more exercise terminals are connected via a communications link to a central computer to form an exercise terminal network. These exercise terminals may include exercise apparatus terminals, exercise station terminals, and exerciser data input terminals. The central computer has a memory for storing a database which includes, inter alia, data regarding the exercisers who use the exercise terminal network. An exerciser may consult with a fitness consultant(s) (e.g., a physician, a physical therapist, or a personal trainer) to develop an exerciser profile and/or to set certain fitness goals. The profile and/or goal data, along with any other desirable data, is entered into the database using, for example, a display (such as a computer monitor) and an input device (such as a keyboard and/or a pointing device such as a mouse or trackball) of the central computer. The data in the database may be used by a system control program of the central computer and/or by the fitness consultant(s) to determine workouts for each exerciser which will best help the exerciser achieve the fitness goals which he/she has set.

The workouts may include the use of one or more of the exercise apparatus terminals in the exercise terminal network. In this regard, the system control program and/or the fitness consultant(s) select exercise data for controlling these one or more exercise apparatus terminals. This exercise data may include an exercise program selection, an exercise time, and/or a difficulty level(s) and is selected based exercise data selection criteria which may include, but is not limited to, one or more of the exerciser's profile data, the exerciser's fitness goal data, and data regarding the exerciser's previous workouts.

The workouts may also include exercises such as stretching, sit-ups, pull-ups, and the like which are performed without using an exercise apparatus or machine. In this regard, the system control program and/or fitness consultant(s) select exercise data such as a number of repetitions and/or a time period for the exercise. Again, this exercise data is based on criteria which may include, but is not limited to, one or more of the exerciser's profile data, the exerciser's fitness goal data, and data regarding the exerciser's previous workouts. For such exercises, the exercise data may be communicated to the exerciser using an exercise station terminal.

Each exerciser using the exercise terminal network is preferably assigned an exerciser identifier such as an exerciser identifier number. An exerciser using a particular exercise terminal enters his/her exerciser identifier using, for example, a numeric keypad. A processor of the exercise terminal uses the entered exerciser identifier to access the database stored at the central computer. In the case of an exercise apparatus terminal, for example, exercise data is retrieved and the processor of the exercise apparatus uses the retrieved exercise data to control the exercise apparatus. In the case of an exercise station terminal, exercise data such as a number of repetitions and an exercise time is retrieved and the processor communicates the exercise data to the exerciser via a speaker and/or a display.

While the exerciser is exercising, one or more physiological-parameters of the exerciser such as heart rate, blood pressure, and the like may be monitored. The system control program and/or the fitness consultant can use such data in order, for example, to select future exercise data, to select the next exercise to be performed in the current workout, and/or to select or vary the exercise data for the next exercise in the current workout.

At the end of an exercise, the exerciser is prompted using aural and/or visual prompts as to which exercise should be performed next or that the current workout is over.

The exerciser may periodically update his/her profile data in the database using one of the exerciser data input terminals connected in the exercise terminal network. These data input terminals may, for example, include a device for measuring some physiological parameter such as weight, heart rate, blood pressure, and the like and a device for communicating these parameters to the database of the central computer. Such updated profile data may be used to determine the effect of the workouts on the exerciser and to select exercise data for future workouts. The profile data may also be updated using an exercise terminal or a computer having a display and an input device(s).

These and other features and advantages of the present invention will be better understood from a reading of the following detailed description in conjunction with the accompanying drawings.

BRIEF DESCRIPTION OF THE DRAWINGS

FIG. 8B is a diagram of a display for exercise station terminal 104b.

FIGS. 11A–11E illustrate various database portions which together constitute at least a portion of the exercise database of the present invention.

FIG. 12 is a table for defining a workout for an exerciser.

DETAILED DESCRIPTION

Figure 3:
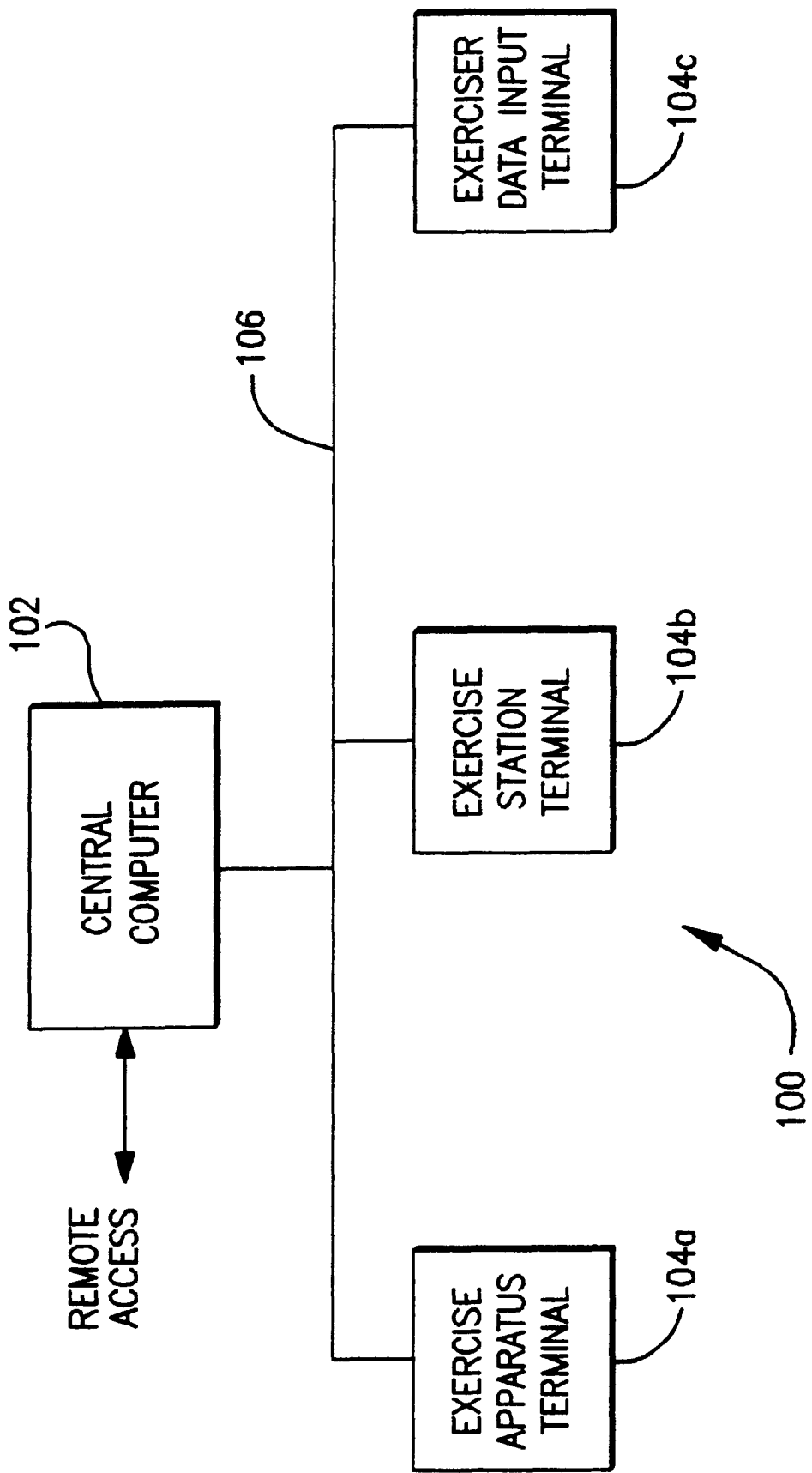
FIG. 3 illustrates an exercise terminal network 100 in accordance with the present invention.

FIG. 3 illustrates an exercise terminal network 100 which includes a central computer (server) 102 and exercise terminals (clients) 104a, 104b, and 104c connected together via a communications link 106. Exercise terminal network 100 may be a local area network (LAN) conforming to any conventional LAN protocol. Communications link 106 may be a twisted pair, a coaxial cable, or an optical fiber, or any other conventional communications link. Exercise terminal network 100 may also be a local area wireless network (LAWN) using radio transmissions in which case communications link 106 is a wireless communications link. Exercise terminal network 100 may also be arranged as a wide area network (WAN), in which case the communications link 106 may include telephone lines. For example, the exercise terminals of a single health club location may be connected together as a LAN or a LAWN, while the exercise terminals of a plurality of health club locations may be connected together as a WAN.

As will be described below, the exercise terminals in exercise terminal network 100 may include, but are not limited to, exercise apparatus terminals 104a, exercise station terminals 104b, and exerciser data input terminals 104c. The present invention is not limited with respect to the type of exercise apparatus terminals 104a which may be incorporated: into network 100. Thus, any exercise apparatus terminal having an exercise device controllable by control circuitry such as a processor in accordance with program data may be incorporated into the network. Such exercise apparatus terminals include by way of example, but not by way of limitation, stationary bicycles, stair climbers, steppers, rowing machines, ski machines, treadmills, cross trainers, and weight machines. Exercise terminal network 100 may also include one or more exercise station terminals 104b. These terminals may be arranged at locations where exercise is performed without the use of an exercise apparatus controlled by control circuitry e.g., free weights, stretching, pull-ups, push-ups, sit-ups, etc. Exerciser data input terminals 104c for supplying exerciser data to central computer 102 may also be incorporated into network 100. For example, an electronic scale may be provided for supplying the weight of exercisers to central computer 102. Other devices for supplying physiological data such as body temperature, blood pressure, heart rate and the like may also be incorporated into exercise terminal network 100 so that such data can be used in the selection of exercise data for an exerciser. While FIG. 3 shows one exercise apparatus terminal, one exercise station terminal, and one exerciser data input terminal connected to central computer 102, it will be appreciated that one or more of any or all of these terminals may be connected in the network 100.

Exercise terminal network 100 is not limited to implementation in health club settings and the exercise apparatus terminals, exercise station terminals, and exerciser data input terminals described above can be provided at the same or at different locations. For example, a single central computer may be linked to terminals in one or more: health clubs, exercisers' homes, hotels, resorts, medical facilities, etc. Thus, for example, an exerciser data input terminal for measuring blood pressure may be provided in an exerciser's home and the blood pressure data communicated to central computer 102 over communications link 106. Fitness consultants may remotely access central computer 102 using a personal computer and a modem, for example, in order to access the exercise database and evaluate the progress of exercisers, as well as to upload exercise data for exercisers. Similarly, exercisers may remotely access the exercise database in order to obtain a record of their exercise activities. Where such remote access to the exercise database is provided, access to the data may be limited. For example, an exerciser might only be given "read" access to the database, while fitness consultants may be given "read/write" access to the database. In some instances, the read/write access of a fitness consultant might be limited to data regarding only those exercisers with whom the consultant is consulting. An exerciser whose weight and other physiological data is communicated to the central computer over communications link 106 may be given "write" access to the fields of the exercise database related to this information. Implementing a database having different access levels using passwords, for example, is well known and will not be described herein. In addition, if an insurance company ("payor") is paying the fees for an exerciser's health membership, the payor may be permitted access to the exercise database to verify the exerciser's use of the health club. For example, claim analysis software of the insurance company may be modified to include a routine which accesses the exercise database to verify the exerciser's use of the health club prior to authorizing payment of a claim for the membership fees. Similarly, if an insurance company is providing an exerciser certain discounts on premiums based on the exerciser's participation in a training routine, the insurance company may be provided access to the exercise database to verify the participation.

Figure 1:
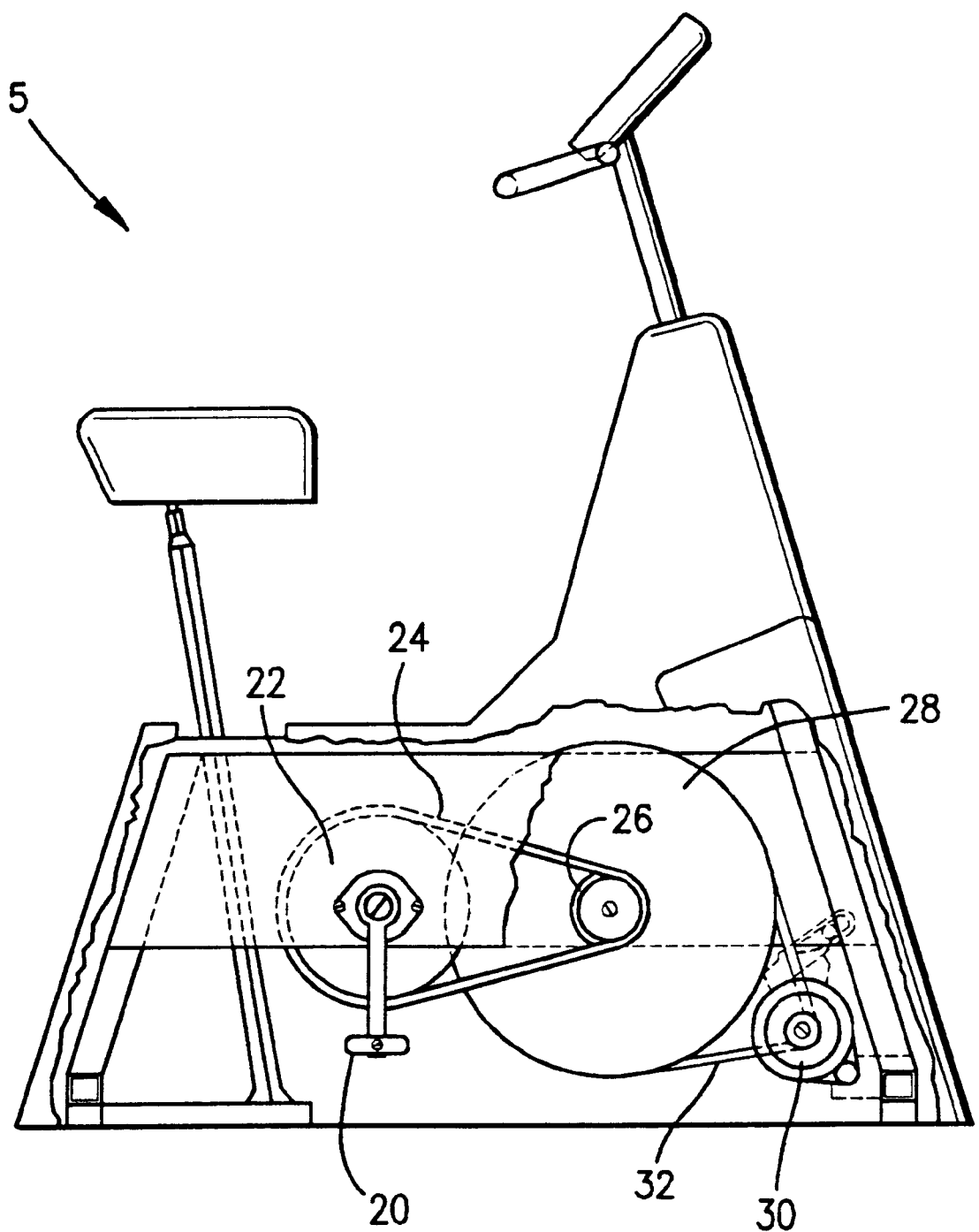
FIG. 1 is a side elevational view of a prior art stationary bicycle 5.
Figure 2:
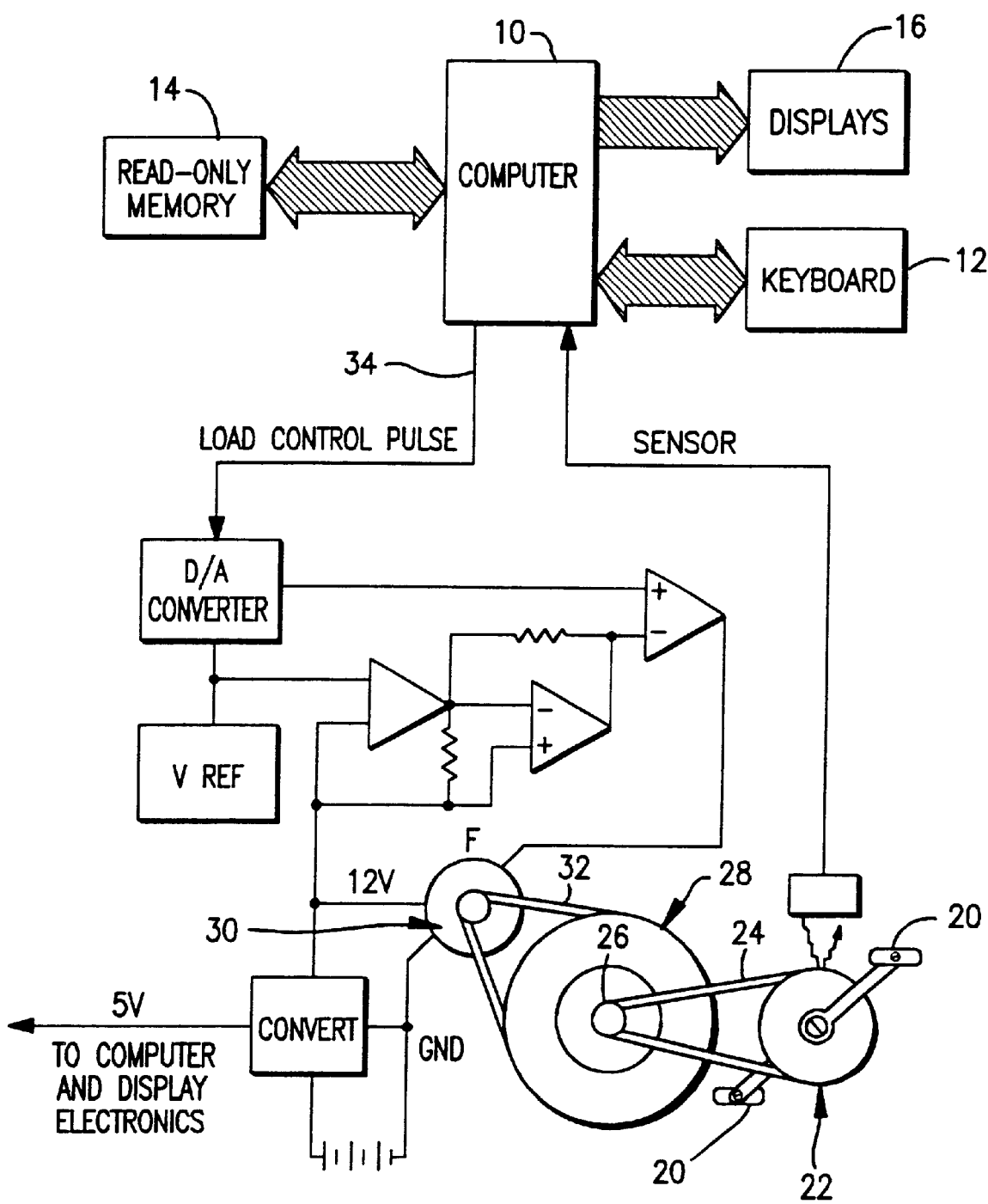
FIG. 2 is a schematic diagram showing the electronic control system of stationary bicycle 5 of FIG. 1.
Figure 4:
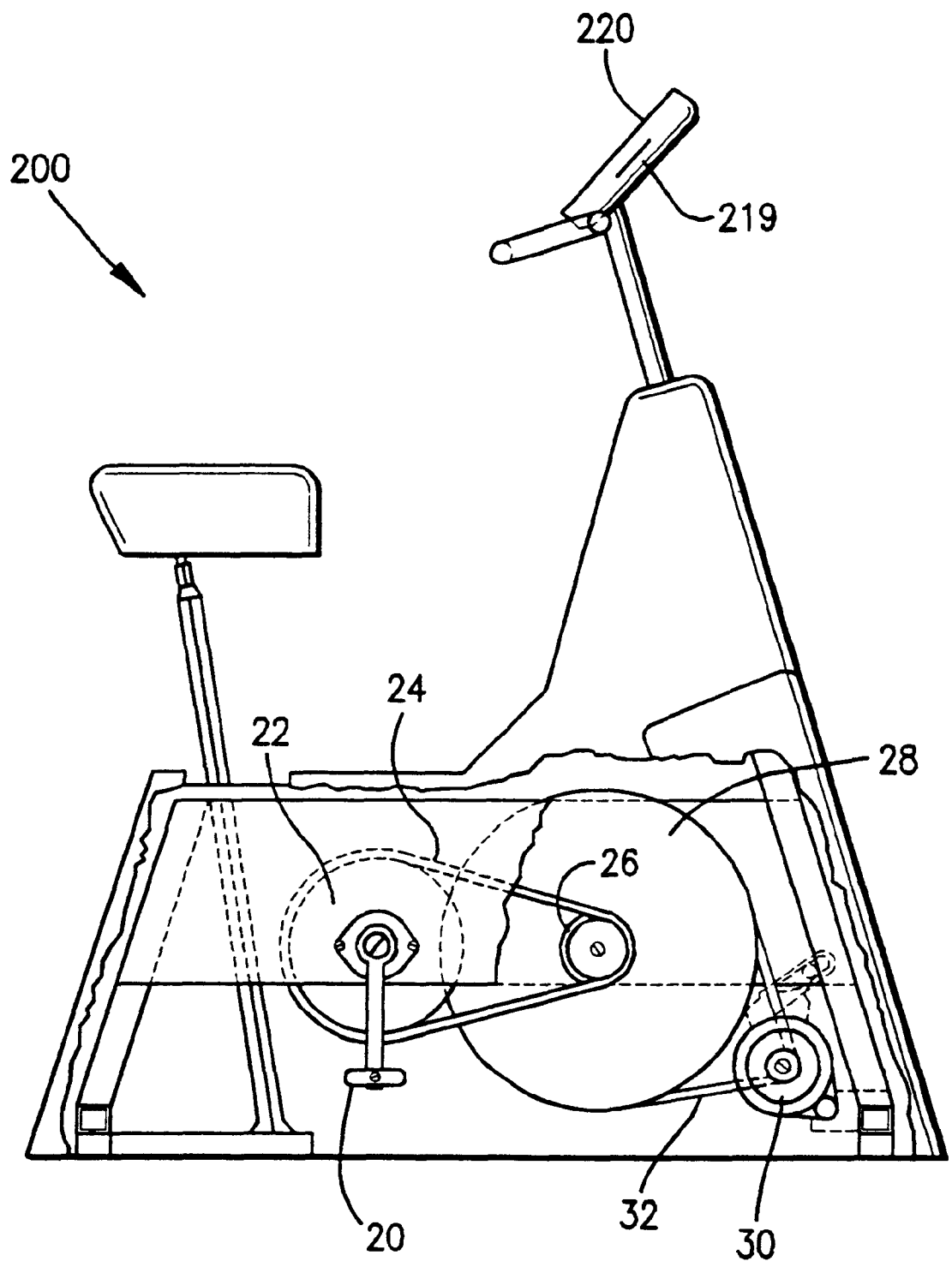
FIG. 4 is a side elevational view of a stationary bicycle 200 which may constitute one of the exercise apparatus terminals 104a in exercise terminal network 100 of FIG. 3.
Figure 5:
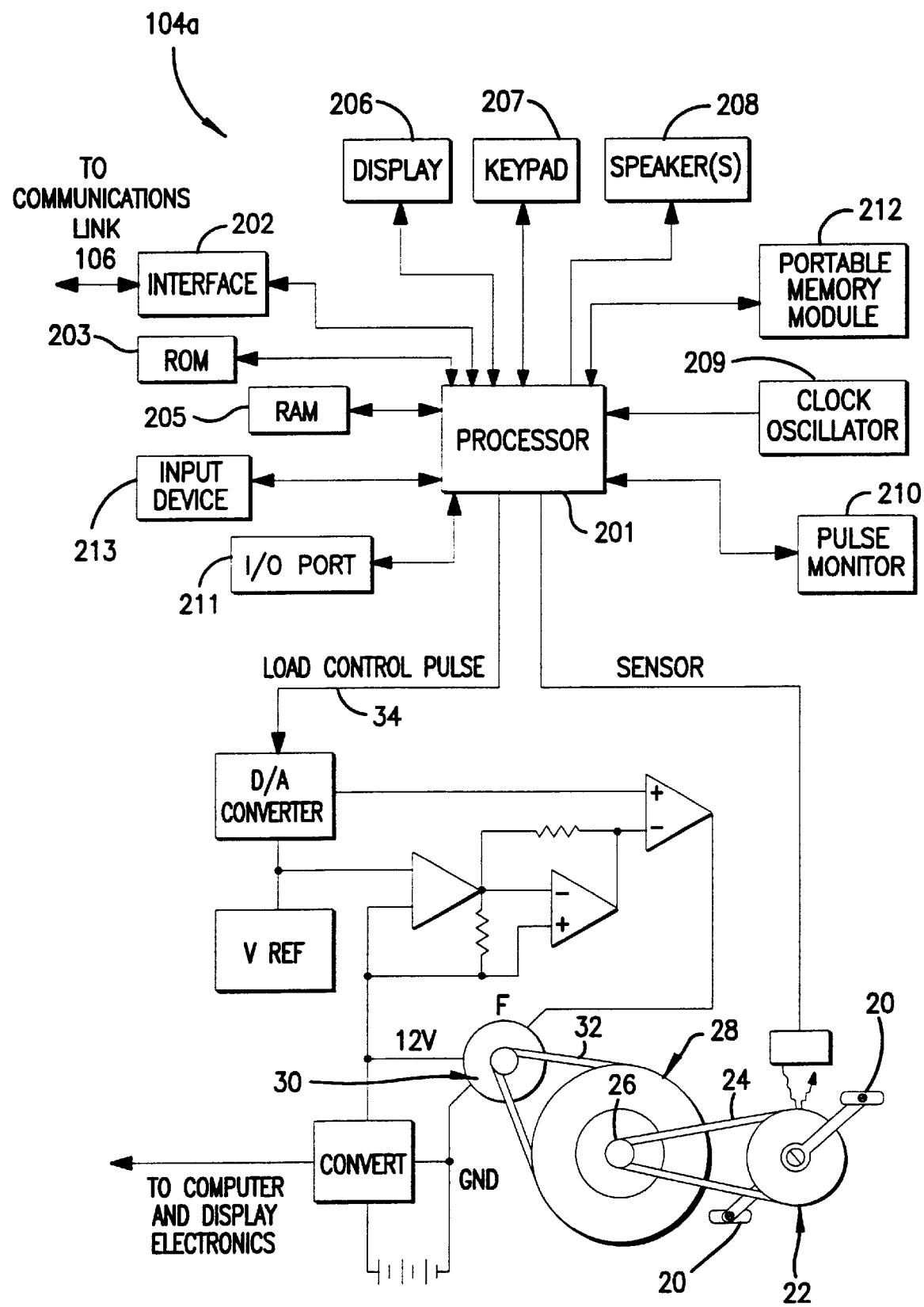
FIG. 5 is a schematic diagram showing the electronic control system of stationary bicycle 200 of FIG. 4.

FIGS. 4 and 5 illustrate a stationary bicycle 200 which may constitute one of the exercise apparatus terminals 104a of exercise terminal network 100. Elements of stationary bicycle 200 which are the same as those of stationary bicycle 5 shown in FIGS. 1 and 2 are designated with the same reference numbers and descriptions thereof are omitted. With reference to FIG. 5, the control system of stationary bicycle 200 includes a processor 201 such as a microprocessor for controlling the operation of stationary bicycle 200; an interface 202; a read-only memory. (ROM) 203 such as an electrically erasable programmable read only memory (EEPROM or $E^2$PROM); a RAM 205; a display 206; a keypad 207; one or more speakers 208; a clock oscillator 209; an optional pulse monitor 210; and an optional input/output (I/O) port 211. Interface 202 controls the transfer of data over the network and may comprise, for example, a modem or a LAN controller and a LAN driver. ROM 203 stores a control program for the stationary bicycle executable by processor 201 and may also contain various pre-stored selectable exercise programs for controlling stationary bicycle 200. Display and keypad panel 220 (see FIG. 4) may include a port 219 (see FIG. 4) which is adapted to receive a portable memory module 212. Portable memory module 212 may be utilized for transferring data to/from ROM 203. Portable memory module 212 may alternatively or additionally store exercise data including exercise programs and/or program parameters (e.g., total exercise time, difficulty level) usable by processor 201 to control stationary bicycle, 200 as described in U.S. Pat. No. 5,947,869, which is incorporated herein by reference. Portable memory module 212 may comprise any convenient portable magnetic or semiconductor memory modules such as $E^2$PROMs, EPROMS, floppy disks, or cards having magnetic strips So-called "smart cards" including both a memory and a microprocessor may also be used. Portable memory module 212 should mate with the control system of stationary bicycle 200 so that processor 201 can read/write data from/to the portable memory module.

Processor 201 generates control signals supplied over line 34 for controlling the exercise level of stationary bicycle 200 in accordance with an exercise program selected from ROM 203 (or from a portable memory module, if provided, as mentioned above) and corresponding exercise program parameters (e.g., total exercise time, difficulty level). If desired, exercise programs for one or more of the exercise apparatus terminals in the exercise terminal network may be stored in the memory of central computer 102. In this case, exercise programs are also selectable from the memory of central computer 102. RAM 205 may be utilized for temporary storage by processor 201. Display 206 includes, for example, a cathode ray tube (CRT), light emitting diodes (LEDs) and/or liquid crystal displays (LCDs) and is responsive to signals from processor 201 for displaying various information to the exerciser including, but not limited to, the elapsed exercise time, the exercise level, the difficulty level number of calories burned, pulse rate, and the like as is known in the art. Keypad 207 includes exerciser-operable keys for inputting various data as will be discussed below. Speaker 208 is responsive to processor 201 for providing audible sounds to the exerciser to indicate, for example, the end of an exercise program or an invalid key press. Clock oscillator 209 provides clocking signals to processor 201 which are used for timing purposes as is well known in the art. These clocking signals may also be utilized by a real time clock algorithm of processor 201 for generating current real time. Pulse monitor 210 may be coupled to processor 201 in order that processor 201 may monitor an exerciser's pulse rate during exercise and provide a display of the monitored pulse rate on display 206. Pulse monitor 210, for example, may be of the wired type having a sensor at a first end which is attached to the exerciser (such as at the ear, wrist, chest, finger, or head) and having a plug at the second end which is plugged into an input jack (not shown) of display and keypad panel 220. Alternatively, pulse monitor 210 may be of the wireless type which is attached to the exerciser and which includes a wireless transmitter for transmitting signals indicative of the exerciser's pulse rate to a wireless receiver (not shown) mounted on display and keypad panel 220. Of course, any type of pulse monitor may be used and the present invention is not limited in this respect. I/O port 211 may be used for inputting/outputting data to/from the control system of stationary bicycle 200. For example, I/O port 211 may be used to connect the control system to an external device including a processor (such as a personal computer) for changing and/or reading the contents of ROM 203. I/O port 211 also may be used to couple stationary bicycle 200 to a television. Display 206 and keypad 207 are arranged on display and keypad panel 220 and are described in greater detail below with reference to FIG. 7. Other input devices (shown generally as 213 in FIG. 5) may also be provided. For example, a bar code orlmagnetic strip reader may be provided in implementations in which an exerciser is provided with a card having his/her exerciser identifier encoded using a bar code or a magnetic strip.

Figure 6:
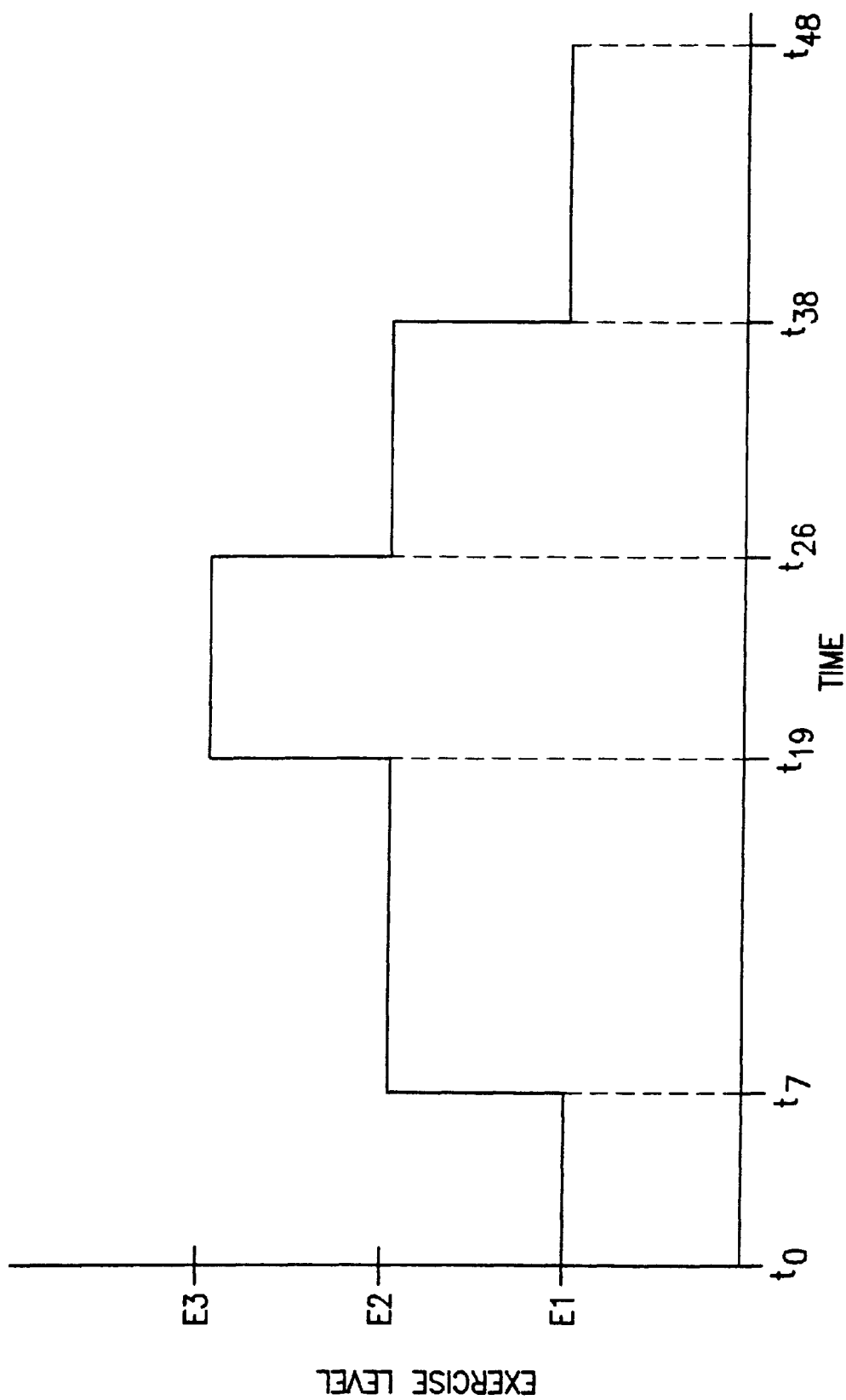
FIG. 6 is a graphical profile of exercise level versus time for an exercise program which may be utilized by processor 201 of FIG. 5 to control the exercise level of stationary bicycle 200.

An exercise program is executable by processor 201 for controlling stationary bicycle 200. FIG. 6 is a graphical profile of exercise level versus time for an illustrative, but non-limiting, exercise program which may be utilized by processor 201 to control the exercise level of stationary bicycle 200 (or some other exercise apparatus terminal). As illustrated in the profile of FIG. 6, from exercise time $t_0$ until exercise time $t_7$, processor 201 generates control signals for setting the exercise level of stationary bicycle 200 to exercise level E1; from exercise time $t_7$ until exercise time $t_{19}$, processor 201 generates control signals for setting the exercise level of stationary bicycle 200 to exercise level E2; from exercise time $t_{19}$ until exercise time $t_{26}$, processor 201 generates control signals for setting the exercise level of stationary bicycle 200 to exercise level E3; from exercise time $t_{26}$ until exercise time $t_{38}$, processor 201 generates control signals for setting the exercise level of stationary bicycle 200 to exercise level E2; and from exercise time $t_{38}$ until exercise time $t_{48}$ (the end of the program), processor 201 generates control signals for setting the exercise level of stationary bicycle 200 to exercise level E1. When a program having the profile of FIG. 6 is selected, a total exercise time over which processor 201 will control stationary bicycle 200 may also be selected. The selection of the total exercise time determines the time interval between the exercise times $t_0$ and $t_1$, $t_1$ and $t_2$, etc. For example, when an exercise program having the profile of FIG. 6 is selected, a total exercise time of four, eight, twelve, sixteen, or twenty minutes may be selected. Depending on which total exercise time is selected, the time interval between the exercise times is five, ten, fifteen, twenty, or twenty-five seconds, respectively. A difficulty level which determines the difficulty of the exercise at the exercise levels of the program may also be selected. The difficulty of exercise levels E1, E2, and E3 is generally less at low difficulty levels than at high difficulty levels. Thus, for example, as the fitness level of an exerciser increases, higher difficulty levels may be utilized. It is possible for an exercise program to have more than one difficulty level associated therewith. For example, the difficulty of a treadmill may be changed by changing either one or both of the tread speed and the incline angle.

The exercise apparatus terminal, portable memory module, and/or central computer preferably store a plurality of exercise programs. These exercise programs may define exercises which range from "easy" to "hard". As can be seen with reference to FIG. 6, an exercise program defines exercise level as a function of time. A first exercise program defining a greater area under the exercise level curve (i.e., the integral of the exercise level from the start time of the exercise until the end time of the exercise) than a second exercise program generally may be viewed as being a "harder" exercise program than the second exercise program. Also, an exercise program executed at a higher difficulty level generally may be viewed as being "harder" than the same exercise program executed at a lower difficulty level. Further, an exercise program which includes one or more peaks of very high exercise levels may be viewed as being "hard", even when compared to another exercise program which defines a greater area under its exercise level curve. It will thus be appreciated features such as these or still other features may be viewed as making one exercise program "harder" or "easier" than another.

Of course, the exercise program of FIG. 6 is for illustrative purposes, and the present invention is not limited to any particular type of exercise program. For example, an exercise program may be of a type which, in addition to varying exercise level as a function of time, provides interactivity via a visual display such as a television or display 206 of the exercise apparatus terminal. for example, the execution of such a program may cause processor 201 to monitor the activity level of the exerciser (e.g., how fast the exerciser is pedaling) via the SENSOR line shown in FIG. 5 and to output data based on this sensed activity level via I/O port 211 to an output device such as a television or to display 206 to thereby simulate a competition between the exerciser and a computer-generated opponent or opponents. Thus, an exercise program for a stationary bicycle may generate a bicycle race between the exerciser and a computer-generated opponent. The "ability" of the opponent and the duration of the race may be set in accordance with the fitness level of the exerciser. In a case where stationary bicycle 200 includes a graphics display controller (not shown) and a modulator (not shown) for outputting a signal on channel 3/4, for example, I/O port 211 may be directly connected to the television. Alternatively, information may be supplied from I/O port 211 to an I/O port of a suitably configured CATV subscriber terminal having a graphics display controller and a modulator to thereby generate a display on a television.

In a first exercise selection mode for an exercise apparatus terminal, an exerciser may select an exercise program, a total exercise time, and/or a difficulty level in a conventional manner. In a second exercise selection mode for an exercise apparatus terminal to be described in greater detail below, an exerciser inputs an exerciser identifier into the exercise apparatus terminal using a keypad and/or some other input device. The processor of the exercise apparatus terminal supplies the input exerciser identifier to central computer 102 in order to access the exercise database and retrieve pre-selected exercise data or in order to generate exercise data. The exercise data for use of an exercise apparatus terminal such as a stationary bicycle may include, but is not limited to, an exercise program identifier, an exercise time, and difficulty level. The exercise program identifier may be used by the processor of the exercise apparatus terminal to access an exercise program stored in a ROM, a portable memory module, or the memory of central computer 102. The processor then executes the selected program in accordance with the corresponding exercise time and/or difficulty level.

Figure 7:
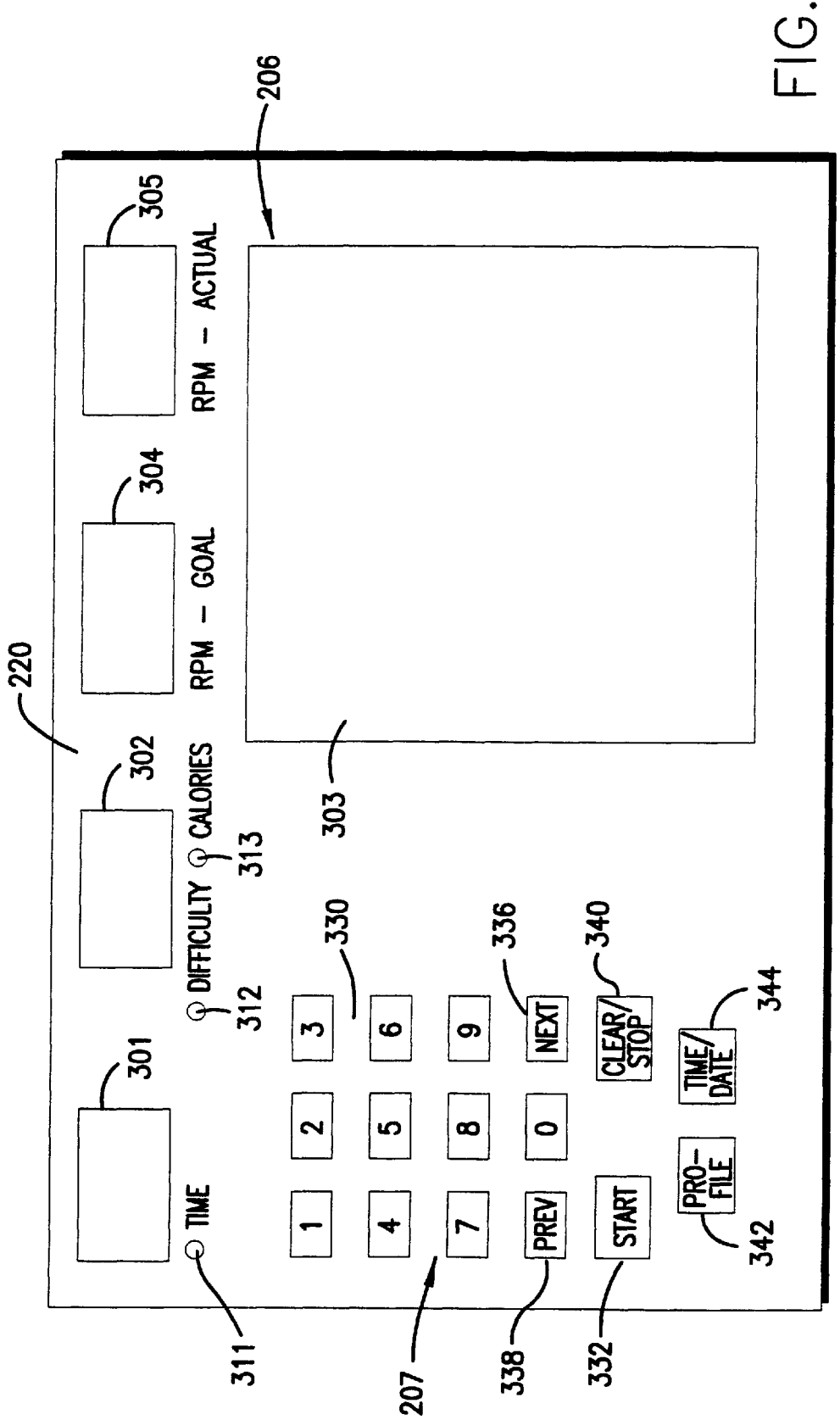
FIG. 7 illustrates display 208 and keypad 210 arranged on display and keypad panel 220 of stationary bicycle 200.

FIG. 7 illustrates display 206 and keypad 207 arranged-on display and keypad panel 220 of stationary bicycle 200. Display 206 includes various display portions 301–305. During the first exercise selection mode, an exerciser may be prompted to enter a total exercise time for an exercise program For example, display portion 301 may display a flashing colon ":" and a time indicator 311 may be illuminated to prompt the exerciser to enter the total exercise time. In addition, during the first exercise selection mode, the exerciser may be prompted to enter a difficulty level for the exercise program. For example, display portion 302 may display a flashing "L" and a difficulty level indicator 312 may be illuminated to prompt the exerciser to enter the, difficulty level. During the second exercise selection mode, display portion 301 displays the total exercise time of the pre-selected or generated exercise data, display portion 302 displays the difficulty level of the pre-selected or generated exercise data, and time indicator 311 and difficulty level indicator 312 are illuminated. During exercise, display portion 301 displays the elapsed exercise time while display portion 302 alternately displays at a predetermined interval (e.g., five or ten seconds) the current difficulty level of the exercise program and the number of calories burned. Difficulty level indicator 312 and a calories burned indicator 313 are appropriately illuminated to indicate which quantity is displayed by display portion 302 during the execution of the exercise program. Time indicator 311, difficulty level indicator 312, and calories burned indicator 313 may be, for example, LEDs. Display portion 303 is a display portion such as an LED display screen, a liquid crystal display screen or a CRT screen for displaying video, textual and/or graphical information to an exerciser. For example, display portion 303 may display program names and descriptions; operating instructions; graphical profiles of exercise level versus time for the exercise program such as is shown, for example, in FIG. 6; and prompts such as the prompts regarding the next exercise terminal to be used as described below with reference to FIGS. 13A and 13B. Display portion 304 provides a display relating to how fast an exerciser should be pedaling stationary bicycle 200 at a current difficulty level and display portion 305 provides a display relating to how fast an exerciser is actually pedaling. Displays of other information may also be provided, if desired. For example, if a pulse monitor 210 is coupled to processor 201, a display portion may be provided for displaying the currently monitored pulse or it may be displayed on display portion 303. Of course, it will be appreciated that the displays of stationary bicycles and other exercise apparatus may be varied in accordance with the apparatus and with the information which it is desired to display and the present invention is not limited in this respect. For example, display 206 may be a single LED display screen, liquid crystal display screen or CRT screen which displays all of the information described above and any other desired information.

Keypad 207 includes a numeric keyboard portion 330 having numeric keys 0–9; a START key 332; a NEXT key 336; a PREV (previous) key 338; a CLEAR/STOP key 340; and a PROFILE key 342. A TIME/DATE key 344 may also be provided. When TIME/DATE key 344 is pressed, the current time and date as maintained by control computer 102 or by the real time clock algorithm of the stationary bicycle are displayed on display portion 303. Alternatively, the time and date may be displayed as part of the display on display portion 303 whenever the stationary bicycle is used. PROFILE key 342 may be used to initiate a routine for entering exerciser profile data as will be described in greater detail below.

As noted above, exercise station terminals 104b are preferably positioned at locations ("or stations") where exercise is performed without the use of an exercise apparatus controlled by control circuitry, e.g., free weights, stretching, pull-ups, push-ups, sit-ups, etc. These exercise station terminals function to provide instructions and feedback to exercisers performing exercise and include an input device such as a keypad, a bar code reader, and/or a magnetic strip reader; a display device such as an LCD screen, an LED screen and/or a CRT screen; one or more speakers; and a control unit such as a processor. An exerciser inputs his/her exerciser identifier into the exercise station terminal using the input device. The processor of the exercise station terminal supplies the input exerciser identifier to central computer 102 in order to access the exercise database of central computer 102 and retrieve pre-selected exercise data or in order to generate exercise data, which exercise data is communicated to the exerciser using the display device and/or the speaker. For example, the exercise data could instruct the exerciser to perform a certain number of pull-ups or sit-ups or lift a certain weight some number of times or perform stretching or some other exercise for some period of time. In the case of a timed exercise, a timer of the exercise station terminal (implemented using the processor and a clock oscillator, for example) may be set to provide the exerciser with a visual and/or aural indication of elapsed exercise time, remaining exercise time, and/or end of exercise time. When the exerciser completes the exercise associated with the exercise station, exercise station terminal 104b may also provide a visual and/or aural prompt as to which exercise terminal should be used next by the exerciser. Of course, one exercise station terminal may be positioned at a location where more than one exercise is performed. That is, one exercise station terminal may be positioned near an exercise mat which is used for stretching, push-ups, sit-ups, etc. and may provide instructions and/or feedback regarding these various exercises. Thus, when a particular exercise is completed, the exercise station terminal may prompt the exerciser to perform another exercise at that sa me location, i.e., stretching may be followed by sit-ups.

Figure 8A:
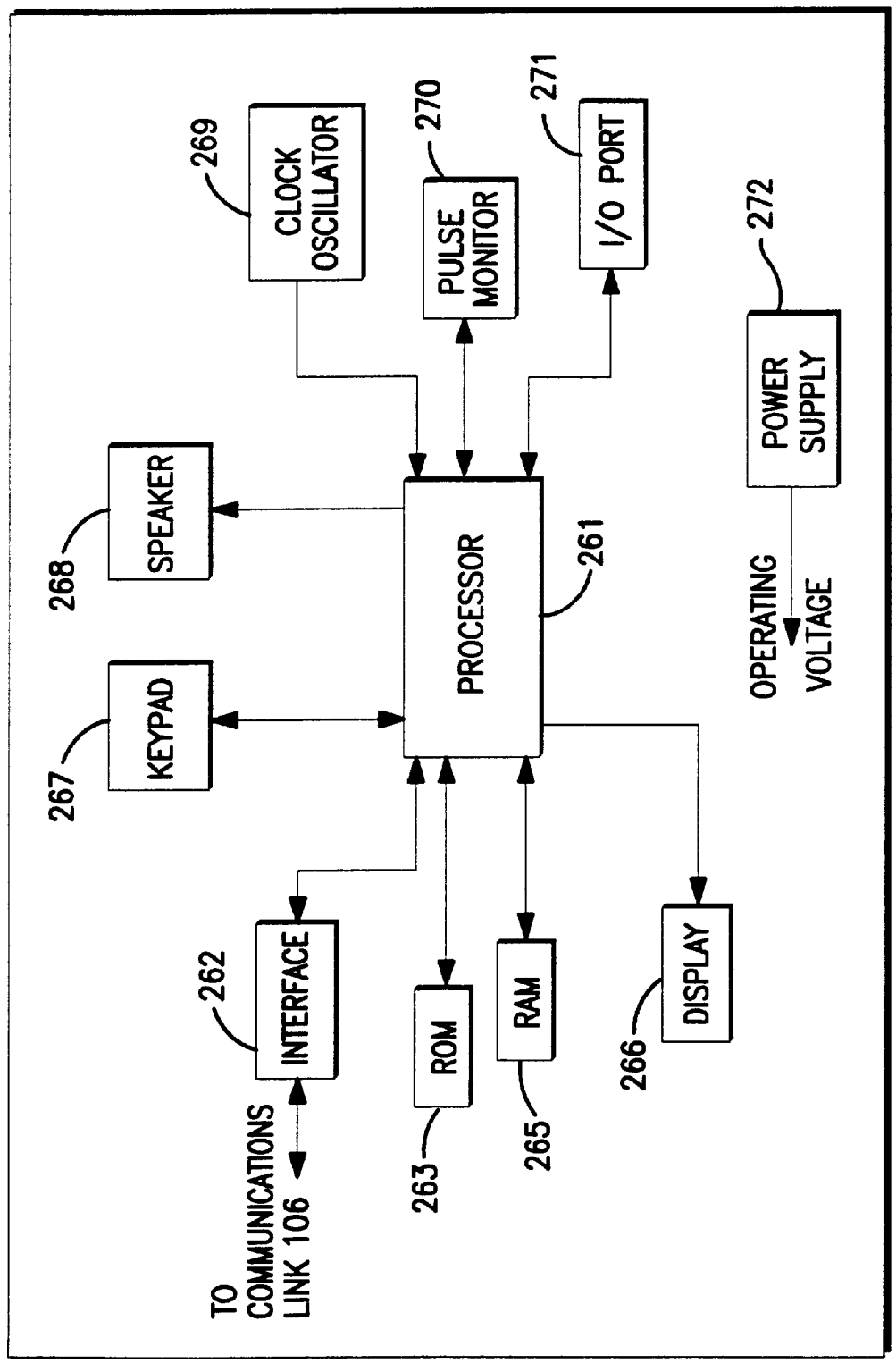
FIG. 8A is a block diagram of an exercise station terminal 104b usable in exercise terminal network 100 of FIG. 3.

FIG. 8A is a block schematic diagram illustrating one of exercise station terminals 104b. Exercise station terminal 104b includes a processor 261 such as a microprocessor for controlling the operation of exercise station terminal 104b; an interface 262; a ROM 263 such as an E²PROM; a RAM 265; a display 266; a keypad 267; a speaker(s) 268; a clock oscillator 269; an optional pulse monitor 270; an optional input/output (I/O) port 271; and a power supply 272. Interface 262 controls the exchange of data over the network and may comprise, for example, modem or a LAN controller and a LAN driver. ROM 263 stores a control program of the exercise station terminal executable by processor 261 and stores other data. RAM 265 is usable by processor 261 for temporary storage. Display 266 such as an LCD screen, an LED screen, and/or a CRT screen is used for displaying instructions or feedback to an exerciser. Keypad 267 is usable by an exerciser for inputting data such as exerciser identifiers into the exercise station terminal. Other input devices (not shown) such as a bar code reader or a magnetic strip reader may also be provided. Speaker 268 is responsive to processor 261 for providing audible sounds to the exerciser to indicate, for example, the end of an exercise or an invalid key press. Clock oscillator 269 provides clocking signals to processor 261 which are used for timing purposes as is well-known in the art. These clocking signals may also be used by timer routines for timing exercise activities as described above or by a real time clock algorithm of processor 261 for generating a current real time. Pulse monitor 270 may be coupled to processor 261 in order that processor 261 may monitor an exerciser's pulse rate during exercise and provide a display of the monitored pulse rate on display 266, for example. I/O port 271 may be used for inputting/outputting data to/from the exercise station terminal, e.g., to/from ROM 263 or to a display device such as a television. Power supply 272 supplies an operating voltage for the operation of the exercise station terminal. The operating voltage may be derived from a battery or from an AC power outlet.

FIG. 8B illustrates a display and keypad panel 292 usable for the exercise station terminal. The panel includes a keypad 293 similar to the keypad described above with respect to FIG. 7 and a discussion thereof is omitted here. The panel further includes a display portion 280 which may be an LCD screen, an LED screen, or a, CRT screen. Display portion 280 is used for displaying instructions or feedback to an exerciser. It will be appreciated that other arrangements of keypads and/or display portions may be utilized and the present invention is not limited in this respect.

Figure 9:
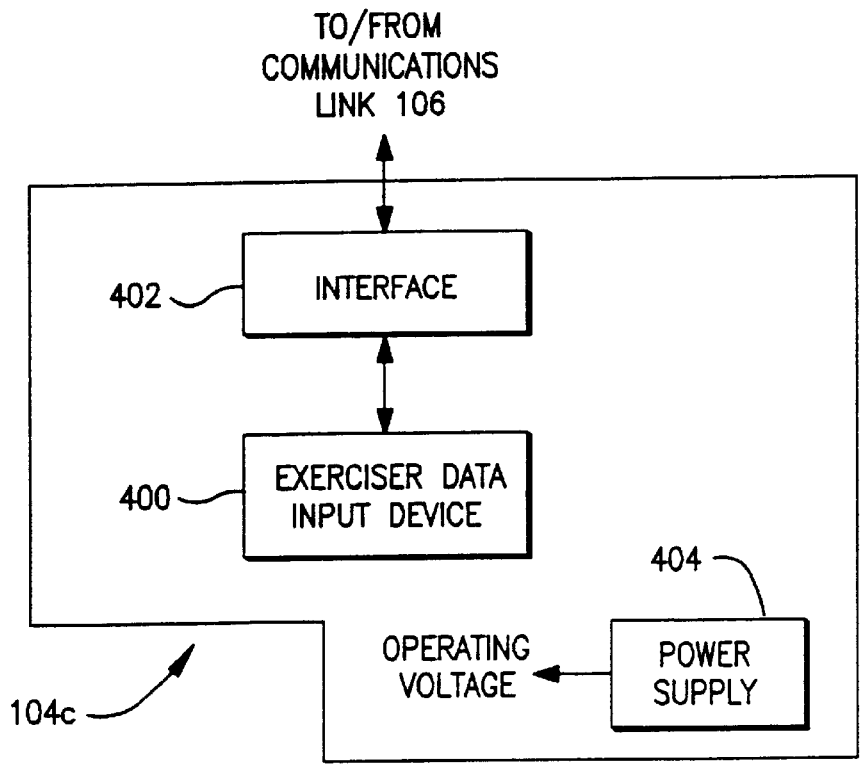
FIG. 9 is a block diagram of an exerciser data input terminal 104c usable in exercise terminal network 100 of FIG. 3.

FIG. 9 is a block diagram of an exerciser data input terminal 104c usable in the exercise terminal network of the present invention. Terminal 104c includes an exerciser data input device 400 for inputting exerciser data. Suitable input devices include, but are not limited to, a scale, a blood pressure device, a pulse rate monitor, a thermometer, and the like. An interface 402 controls the transfer of data to/from input device 400, over the-network. Such an interface may be a modem, a LAN controller and LAN driver, and the like. A power supply 404 supplies an operating voltage for the operation of the exercise data input terminal. The operating voltage may be derived from a battery or from an AC power outlet.

Figure 10:
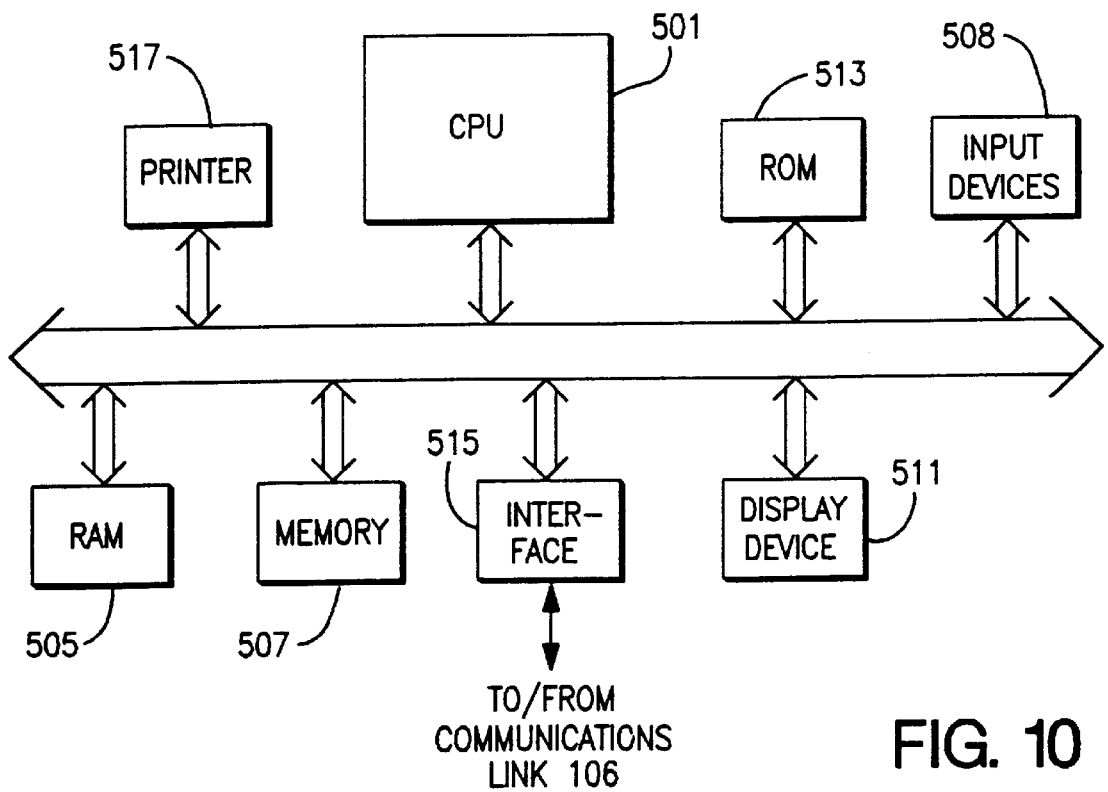
FIG. 10 is a block diagram of central computer 102 of exercise terminal network 100 shown FIG. 3.

FIG. 10 is a block diagram of central computer 102. Central computer 102 may, for example, be an IBM®-PC compatible personal computer. It should be understood that central computer 102 is not limited to any particular type or brand of computer, and thus contemplates microcomputers to supercomputers. Central computer 102 includes a central processing unit (CPU) 501 such as an IBM® PC-compatible CPU which is plugged into bus 503. The system control program is loaded into memory (RAM) 505 during operation. Memory 507 stores data which is accessible by CPU 501. Memory 507 can be any standard memory device or combination of memory devices such as a semiconductor memory, a magnetic disk, a magnetic tape, or an optical memory such as a CD-ROM. Central computer 102 further includes input devices, generally shown as 508, such as a keyboard, a mouse, a touchpad, a touchscreen, a scanner, or any compatible or equivalent device. A visual display device 511 such as a CRT is provided. Other output devices may include a printer 517, speakers, etc. A ROM 513 may store certain programs (e.g., a BIOS) and configuration parameters for central computer 102. ROM 513 may be an E²PROM for example, to allow for the updating of this information. The system control program and the database of exercise network 100 may be stored in memory 507. Interface 515 such a network control card or modem controls the transfer of information over the network.

FIGS. 11A–11E illustrate various database portions which together constitute the exercise database for exercise terminal network 100. The database portions are stored in memory 507 (e.g., a semiconductor memory such as an E²PROM, a magnetic memory such as a hard drive or a floppy disk, or an optical memory such as a CD-ROM) of central computer 102 of exercise terminal network 100. Of course, the organization of data shown in FIGS. 11A–11D is for exemplary purposes only and the present invention is not limited in this respect.

FIG. 11A shows an exerciser database portion which is organized by exerciser identifier and stores exerciser data relating to the exercisers using exercise terminal network 100. Specifically, the exerciser database portion includes, but is not limited to, some or all of the following data for each exerciser: a unique exerciser identifier such as an exerciser identifier number; the name, postal address (e.g., number, street, city, state, and zip/postal code), and telephone number(s) (e.g., home, work, and/or facsimile) of the exerciser; the electronic mail (e-mail) address of the exerciser; messages for the exerciser from, for example, the system administrator or the exerciser's fitness consultant; profile data regarding the exerciser and the exerciser's goals which will be used in the selection of exercise data; future exercise data; and previous exercise data. It will be appreciated that each data item which is identified as being stored in the exerciser database portion and the other database portions which constitute the exercise database may comprise one or more data fields or one or more data tables. For example, the "name" stored in the database portion of FIG. 11A may comprises a first name field, a last name field, a middle initial field, etc. Generally, the data in the database portion of FIG. 11A would be collected during a meeting or meetings with a fitness consultant.

The profile data may include the exerciser's height, weight, age, and an indication of current fitness level. The fitness level may be determined by having the exerciser perform some exercise while certain physiological parameters such as heart rate and/or blood pressure are monitored. In this way, some general determination may be made as to what exercise data should be selected for the initial workouts of the exerciser. The exerciser may also be asked whether he/she has any specific exercise goals. In this way, exercise data may be selected to assist the exerciser in achieving these goals. For example, an exerciser may be interested in achieving a goal of weight loss or cardiovascular fitness. Based on one or both of these goals and the exerciser's age, the proper range for the pulse rate of the exerciser during exercise may be determined by the system control program of central computer 102 or the fitness consultant. Specifically, the exerciser's maximum heart rate may determined by subtracting the exerciser's age from 220. From this, the appropriate pulse rate during exercise may be determined as between about 65% and about 75% of the maximum pulse rate for fat loss and between about 75% and about 90% for cardiovascular fitness. Alternatively, a range in which the exerciser's pulse rate should be maintained during exercise may be directly entered into the exercise profile. Such a pulse rate range may, for example, be determined by a physician. The profile may also include other fitness goals of an exerciser, e.g., training to run a ten kilometer race, a marathon, weight training'cycling, tennis, golf, skiing, etc. If the exerciser is training for an event such as a race on a particular date, this event date may also be entered. The system control program of central computer 102 and/or the fitness consultant may utilize this information in order to factor such desired fitness goals into the selection of the exercise data. That is, the system control program and/or the fitness consultant may select exercise data best suited to assist the exerciser in achieving his/her goal by a particular date. Dates for, achieving other goals such as weight loss may be included in the profile. For example, an exerciser may indicate a goal to lose ten pounds over a three month period (about one pound a week). The system control program and/or a fitness consultant can then select exercise data to assist the exerciser in losing the ten pounds over the three month period. By monitoring the exerciser's weight throughout the three month period using an exerciser data input terminal 104c, the system control program and/or fitness consultant can, for example, select harder or longer exercises if the exerciser is not making sufficient progress toward the weight loss goal.

The profile data may also include an indication of how many calories an exerciser desires to expend during a typical workout. The system control program and/or a fitness consultant can then select exercise data which is designed to cause the exerciser to expend the desired number of calories.

The profile data of an exerciser may be periodically updated using an appropriate exercise data input terminal, an exercise apparatus terminal, an exercise station terminal, or a computer within or linked to the network. For example, the exerciser's weight may be periodically entered into the database to permit the exerciser to determine how the workouts are affecting weight loss if weight loss is a desired goal. Similarly, the exerciser's resting and-training pulse rate and resting and training blood pressure may be periodically entered into the database to provide a further indication of how the workouts are impacting on the exerciser's fitness. In addition, the particular fitness goals of the exerciser (e.g., a ten kilometer race, marathon, etc.) may be periodically updated. In general, the profile data of an exerciser may include any information which it is desired to utilize in the selection of exercise data.

The future exercise data determines workouts for an exerciser. Each exercise in a workout may include, but is not limited to, some or all of the following data: a sequence number; an exercise identifier; an exercise terminal type identifier identifying the type of exercise terminal at which the exercise is performed; and exercise parameters (such as total exercise time, difficulty level(s), etc.) for setting parameters of the exercise. As will be described in greater detail below, the future exercise data may be pre-selected by the system control program and/or a fitness consultant or may be dynamically generated or varied by the system control program.

The previous exercise data is a record of the workout activities of an exerciser and may include, but is not limited to, some or all of the following data: exercise terminal used; exercise performed; initial difficulty level; initial total exercise time; final difficulty level; final total exercise time; certain physiological data such as pulse rate at one or more times during exercise; a flag indicating whether the exercise was completed; and an indication of the exerciser's feelings about the exercise (e.g. "1"=too hard, "2"=too easy, "3"= about right).

The database portion of FIG. 11B is an exercise terminal database portion which is organized by exercise terminal identifier (or address) and contains data regarding the exercise terminals in exercise terminal network 100. For example, for each exercise terminal in exercise network 100, the exercise terminal database portion may include, but is not limited to, some or all of the following data: an exercise terminal identifier (or address); exercise terminal type data; exercise terminal purchase data; exercise terminal use data; exercise terminal location data; exercise terminal maintenance data; and exercise terminal manufacturer data. The exercise terminal type data may include exercise terminal type identifiers for identifying an exercise terminal as a stepper, a stationary bicycle, a station for stretching, a station for pull-ups, a data input terminal for weight, etc. The exercise terminal purchase data may include, but is not limited to, terminal owner data, the terminal purchase date, and the terminal price. The exercise terminal maintenance data may include, but is not limited to, data regarding previous maintenance checks (maintenance check dates, maintenance tests performed, problems fixed, etc.) and a schedule for future maintenance checks. The exercise terminal use data may include, but is not limited to, a count of the number of times the terminal has been used. Such terminal use data can provide valuable information to health club operators as to which exercise terminals are popular with exercisers and which are not. The use data may also be utilized in the determination, either automatically by the system control program or by the system administrator, of a schedule for future maintenance checks. The exercise terminal location data may include, but is not limited to, a postal address of the building in which the terminal is located and data identifying the location of the terminal within a particular building. This latter data is used to provide the location information provided to an exerciser regarding the next exercise terminal to be used as described below with respect to FIGS. 13A and 13B. The location data can include text string data such as "by the back wall" or "next to the free weights". The location data can also include data used in generating video, animated, and/or graphical displays indicating the location of the exercise terminal relative to other exercise terminals and/or features at a particular location. The terminal manufacturer data may include, but is not limited to, terminal model data (model name, model number, etc.), manufacturer name, manufacturer postal address, manufacturer telephone number, manufacturer facsimile number, warranty information, etc.

The database portion of FIG. 11C is an exercise database portion organized by exercise identifier for identifying exercises "Exercise" may refer to an exercise program which is executable by a processor of an exercise apparatus terminal, in which case the exercise identifier is an exercise program identifier for identifying an exercise program "Exercise" may also refer to an exercise which is performed without the use of an exercise apparatus controlled by a processor. In this case, the exercise identifier identifies an exercise such as stretching, pull-ups, etc. Thus, for example, a first exercise identifier may identify the exercise program of FIG. 6, a second exercise identifier may identify sit-ups, etc. For each exercise, this database portion may include, but is not limited to, some or all of the following data: an exercise identifier; an exercise type identifier; an exercise description; program profile data for generating a graphical display of exercise level versus time such as that shown in FIG. 6, if appropriate; and program parameters. The exercise type identifier identifies the exercise as an exercise program executable by a processor or an exercise to be performed at an exercise station terminal (i.e., an exercise performed without the use of an exercise apparatus under the control of control circuitry). The exercise description may include a textual description of the exercise (e.g., sit-ups). In some cases, the exercise description may include data for generating a video, graphical and/or animated display (along with accompanying audio, if desired) regarding the exercise. This display and accompanying audio may be communicated to the exerciser using the display and speakers of the exercise terminal. The display and audio may indicate the proper way of performing the particular exercise, the muscles or muscle groups worked during the exercise, etc. The audio and video may be presented to the exerciser in response to a particular key press, for example. The profile data may be used to generate a graphical display of exercise level versus time which may be used by a fitness consultant or the exerciser in the selection of exercises. The parameters define the parameters which are used for the exercise. For example, the parameters for the exercise "sit-ups" may include a number parameter for the number of sit-ups and a time parameter for the time within which the sit-ups should be completed. The parameters for an exercise program executable by a stationary bicycle may include a total exercise time parameter and a difficulty level parameter.

The database portion of FIG. 11D determines which exercises can be performed at each exercise terminal type. Thus, the database portion of FIG. 11D relates exercise identifiers and exercise terminal type identifiers. It is possible for two exercises (e.g., sit-ups and stretching) to be associated with the same exercise terminal type. It is also possible for one exercise (such as the exercise program of FIG. 6) to be associated with more than one exercise terminal type (e.g., steppers of different manufacturers or a stepper and a stationary bicycle).

In a first implementation of the present invention to be described below, exercise data for a workout is pre-selected for an exerciser and stored in the exercise database as the future exercise data. This pre-selection of exercise data for a workout may be performed by, for example, an exercise selection routine of the system control program of central computer 102, a fitness consultant, or even the exerciser himself/herself. A workout comprises one or more exercises to be performed by an exerciser. In general, the exercise data for each exercise includes, for example, a sequence number; an exercise identifier; an exercise terminal type identifier identifying the type of exercise terminal at which the exercise is performed; and exercise parameters for the exercise (e.g., a total exercise time, a difficulty level, a number of repetitions, and the like). As will be described in greater detail below, the system control program of the present invention uses the sequence numbers associated with exercises to guide an exerciser through a workout by providing, for example, aural and/or visual prompts which inform the exerciser which exercise terminal type or which specific exercise terminal should be used next in the workout.

In a second implementation of the present invention, exercise data for a workout is at least partly based one or more factors which are evaluated during a workout, such as an exerciser's performance during one or more exercises in the current workout; the availability or unavailability of certain exercise terminals for use by the exerciser; an indication by an exerciser as to certain physical limitations (e.g., the exerciser has a sore shoulder and cannot perform certain weight lifting exercises); an indication by an exerciser as to certain time limitations (e.g, the exerciser has only 45 minutes to complete the workout); the burning of a particular number of calories; and the like. Using such factors, the system control program can dynamically determine a workout for an exerciser or can modify a pre-selected workout for an exerciser.

A description of the first implementation will now be described with reference to the workout for a particular exerciser defined by the exercise data of FIG. 12. The exercise data of FIG. 12 defines a workout in which an exerciser performs three exercises: stretching, pedaling a stationary bicycle, and using a stepper. As can be seen, each exercise is defined by a sequence number; an exercise identifier; an exercise terminal type identifier identifying the type of exercise terminal at which the exercise is performed; and exercise parameters for the exercise. The sequence number includes a workout sequence portion and an exercise sequence portion. The workout sequence portion identifies a particular workout and the exercise sequence portion identifies a particular exercise within the workout. For example, the stretching exercise of FIG. 12 is designated by a workout sequence number of 1-1 which indicates that stretching is the first exercise of workout number 1. The stationary bicycle exercise is designated by a workout sequence number of 1-2 which indicates that the stationary bicycle is the second exercise of workout number 1. Finally, the stepper exercise is designated by a workout sequence number of 1-3 which indicates that the stepper is the third exercise of workout number 1. The exercise identifier identifies one of the exercises in the database portion of FIG. 11C. The exercise terminal type identifier identifies the type of exercise terminal at which the exercise is performed (e.g., a stretching station terminal, a stationary bicycle, a stepper). The exercise parameters may include parameters such as total exercise time, difficulty level(s), number of repetitions, etc. With specific reference to the exercise data of FIG. 12, the first exercise, stretching, is defined by a workout sequence number of 1-1; an exercise identifier of 01 (which will be assumed to identify "stretching" as the exercise); an exercise terminal type identifier of 01 (which will be assumed to identify an exercise terminal for stretching exercises as the exercise terminal to be used); and a time parameter of 5:00 minutes which defines how long the exerciser should stretch. The second exercise, pedaling a stationary bicycle, is defined by a workout sequence number of 1-2; an exercise identifier of 02 (which will be assumed to identify an exercise program stored in ROM 203 of the stationary bicycle which is executable by processor 201); an exercise terminal type identifier of 02 (which will be assumed to identify a stationary bicycle); a total exercise time parameter of 12 minutes; and a difficulty level parameter of 8. The third exercise, using a stepper, is defined by a workout sequence number 1-3; an exercise identifier 03 (which will be assumed to identify an exercise program stored in the ROM of the stepper which is executable by the processor of the stepper); an exercise terminal type identifier of 07 (which will be assumed to identify a stepper); a total exercise time parameter of 8 minutes; and a difficulty level parameter of 9. At the end of each exercise in the workout, the system control program uses the workout sequence number to determine the next exercise in the workout. The system control program then'uses the exercise terminal type identifier associated with this next exercise to prompt the exerciser as which exercise terminal should be used next in the workout. For example, at the end of stretching, the system control program determines that the next exercise uses a stationary bicycle. Similarly, at the end of the exercise using the stationary bicycle, the system control program determines that the next exercise uses a stepper. Finally, at the end of the exercise using a stepper (the last exercise in workout sequence number 1), the system control program determines that the workout is over. If desired, the exercise data of FIG. 12 may be modified to include an exercise terminal identifier whereby a specific exercise terminal (e.g., a specific stationary bicycle or a specific stepper) is identified for use by the exerciser.

To begin the workout, the exerciser enters his/her exerciser identifier at the exercise station terminal for stretching using, for example, a numeric keypad of the exercise station terminal. Processor 261 uses the entered exerciser identifier to retrieve the appropriate pre-selected exercise data for the exerciser from the exercise database which, in this case, is the exercise identifier for stretching and the total exercise (stretching) time of 5:00 minutes. The exerciser is provided with a prompt which indicates the exercise (stretching) and the total exercise time. If the total exercise time is acceptable to the exerciser, he/she may begin to exercise. The exerciser may, if desired, change the total exercise time. A video, graphical and/or animated display suitable for the total exercise time may be provided for the exerciser to follow. When the total exercise time has: elapsed, the exercise database is updated with any desired exercise data (such as exercise time, pulse rate at one or more times during the exercise, etc.) and the exerciser is provided with an aural and/or visual prompt regarding the next exercise terminal to be used based on the next exercise in the workout as determined with reference to the exercise sequence number. In this case, the exerciser is provided with an aural and/or visual prompt which identifies a stationary bicycle such as stationary bicycle 200 as the next exercise terminal to be used. The prompt may be provided in the manner described below with reference to FIGS. 13A and 13B. The exerciser then proceeds to the stationary bicycle and enters his/her exerciser identifier using, for example, the numeric keypad. Processor 201 uses the entered exerciser identifier to retrieve exercise data from the exercise database. In this case, the retrieved exercise data includes the exercise identifier 02, a total exercise time parameter of 12:00 minutes, and a difficulty level parameter of 8. The exercise identifier 02 identifies an exercise program which is executable by the processor of the stationary bicycle. If the exercise program corresponding to the retrieved exercise identifier, the total exercise time, and the difficulty level are acceptable to the exerciser, he/she may begin to exercise. The exerciser may, if desired, change one or more of these exercise data items. Upon completing the exercise, the exercise database is updated with any desired exercise data regarding the exercise and the stationary bicycle prompts the exerciser using the display and/or the speaker(s) that the stepper is the next exercise terminal to be used in the workout. This prompt may be provided in the manner described below with reference to FIGS. 13A and 13B. The exerciser then proceeds to the stepper and enters his/her exerciser identifier using, for example, the numeric keypad. Processor 201 uses the entered exerciser identifier to retrieve exercise data from the exercise database. In this case, the retrieved exercise data includes an exercise identifier 03, a total exercise time parameter of 8:00 minutes, and a difficulty level parameter of 9. The exercise identifier 03 identifies an exercise program which is executable by the processor of the stepper. If the program corresponding to the retrieved exercise identifier, the total exercise time, and the difficulty level are acceptable to the exerciser, he/she may begin to exercise. The exerciser may, if desired, change one or more of these exercise data items. Upon completing the exercise, the exercise database is updated with any desired exercise data regarding this exercise and the exerciser is visually and/or aurally prompted that the workout is over. The prompt may, for example, be "Congratulations! Your workout is over." The prompt may also include workout summary information such as exercises performed, total calories burned during the workout, and the like. If desired, the exerciser may (by using the keypad of the last exercise terminal used in the workout, for example) cause a print-out to be printed by printer 517 which identifies the exercises performed during the workout, the total number of calories burned, pulse rate during the exercises, etc.

In the second implementation, the exerciser begins the workout at an exercise terminal for stretching in order to warm-up. The exerciser enters his/her exerciser identifier using, for example, a numeric keypad of the exercise terminal. The system control program then uses the entered exercise identifier to access the exercise database and evaluate factors such as the previous exercise data of the exerciser; when the exerciser last exercised; and/or any other desirable factors in order to determine the parameters for exercise at the current terminal. For example, the system control program may determine that the exerciser should perform five minutes of stretching as a warm up. At the end of the five minutes of stretching, the system control program then determines a next exercise to be performed by the exerciser. The exercise is defined in the same manner as the exercises of FIG. 12. Specifically, the system control program generates and stores in the exercise database an appropriate workout sequence number, an exercise identifier, an exercise terminal type identifier, and exercise parameters. The exerciser is provided with an aural and/or visual prompt as to the exercise terminal type at which this next exercise is to be performed. Similar to the first implementation, an exercise terminal identifier may be generated whereby a specific exercise terminal is identified for use by the exerciser. In this case, assume the exerciser is prompted to use a treadmill. The exerciser then proceeds to a treadmill and enters his/her exerciser identifier using, for example, a numeric keypad. The control system of the treadmill accesses the generated exercise identifier, total exercise time, and difficulty level(s) and displays these exercise data items to the exerciser. If these exercise data items are acceptable to the exerciser, he/she may begin exercise. If desired, the exerciser may modify one or more of the exercise data items prior to exercise. At the end of the exercise using the treadmill, the system control program determines whit, if any, exercise should be performed next by the exerciser. This determination may be based on factors including a total number of calories burned, a total predetermined time during which the exerciser's heart rate is a zone appropriate for achieving a particular fitness goal and the like. For example, if the exerciser is having difficulty with a current exercise, the system control program may determine that the next exercise is an easy exercise. The exerciser's difficulty with a current exercise may be determined based on one or more of the following: the CLR/STOP key was used to prematurely end the current exercise; the exerciser has lowered the difficulty level during the current exercise; the exerciser indicates he/she found the current exercise too hard; and physiological parameters (such as pulse rate) measured during the current exercise indicate the exerciser is having difficulty.

Similarly, if the current exercise is too easy for an exerciser, the system control program may determine that the next exercise is a hard exercise. The ease of the current exercise may be determined based on one or more of the following: the exerciser increased the difficulty level during the current exercise; the exerciser indicates he/she found the current exercise too easy; and physiological parameters (such as pulse rate) measured during the current exercise indicate the exerciser is not exercising at a high enough exercise level.

In these cases, the system control program can use this information to dynamically select a next exercise as described above. Alternatively, this information can be used to vary the exercise data which was preselected by the system control program or a fitness consultant. In this way, for example, an exerciser can avoid overexertion or injury which might result from attempting to complete a workout which is beyond his/her current fitness level. In addition, such a dynamic workout determination or modification can avoid psychological effects which might be associated with failing to complete a workout. That is, if the system control program "eases up" or ends a workout based on an exerciser's performance on a given day, the exerciser can still have a feeling that he/she accomplished what he/she should have. This provides a positive feedback encouraging the exerciser to return for his/her next workout. In the case of making the next exercise a hard exercise, the exerciser who is finding a workout too easy is able to obtain the benefits of a workout better suited for his/her fitness level.

Other factors may also be used in the dynamic determination of next exercises or the varying of pre-selected exercise data. One such factor is the availability of exercise terminals. For example, if no steppers are currently available, the system control program can prompt the exerciser to use a terminal which is currently available. This avoids the "cooling down" (and frustration) of an exerciser who is waiting for a terminal of a particular type to be free.

Of course, it should be kept in mind that the system control program or fitness consultant may desire to provide "hard" and "easy" workouts for an exerciser. Thus, an exerciser's indication that he/she finds a particular exercise to be too hard/too easy may not always be used as a factor in determining or varying the next exercise to be performed. However, for example, where an exerciser is clearly struggling (e.g., the difficulty level is significantly lowered from an initial difficulty level or an exercise is stopped after only a very short period of time by pressing the CLR/STOP key), such factors may advantageously be considered in the determination or variation of a next exercise to be performed.

As noted above, the exercise system provides an identification on the display of an exercise terminal (e.g., on display portion 303 of stationary bicycle 200 shown in FIG. 7 or display portion 280 of FIG. 8B) which identifies for the exerciser the exercise terminal to be used next in the workout. Such an identification may include a textual identification such as "NEXT EXERCISE TERMINAL: STEPPER", "NEXT EXERCISE TERMINAL: TREADMILL", or "NEXT EXERCISE TERMINAL: FREE WEIGHTS". In a health club setting in which there are more than one exercise terminal of the same type, the textual identification provided on the display of the exercise terminal can, if desired, be more specific such as "NEXT EXERCISE TERMINAL: STEPPER #2", "NEXT EXERCISE TERMINAL: TREADMILL #3", or "NEXT EXERCISE TERMINAL: FREE WEIGHTS #2". In such a health club setting, the exercise terminals may have tags or labels associated therewith which identify them by number. Of course, the exercise terminals may have tags or labels with identifiers other than numbers and such other identifiers could be provided as part of the textual identification on the display. The prompt may also include location information regarding the location of the next exercise terminal to assist the exerciser in locating the terminal. For example, the prompt could be "NEXT EXERCISE TERMINAL: STEPPER ALONG BACK WAIL" or "NEXT EXERCISE TERMINAL: TREADMILL BY WINDOW". The prompt could also be in the nature of "NEXT EXERCISE TERMINAL: STEPPER TO YOUR LEFT" or "NEXT EXERCISE TERMINAL: TREADMILL BEHIND YOU". Of course, the present invention is not limited to the above-described examples of textual identification. In general, the textual identification may be any information which provides meaningful guidance to the exerciser with regard to the identification of an exercise terminal to be used next by the exerciser and/or the location of an exercise terminal to be used next by the exerciser.

Figure 13A:
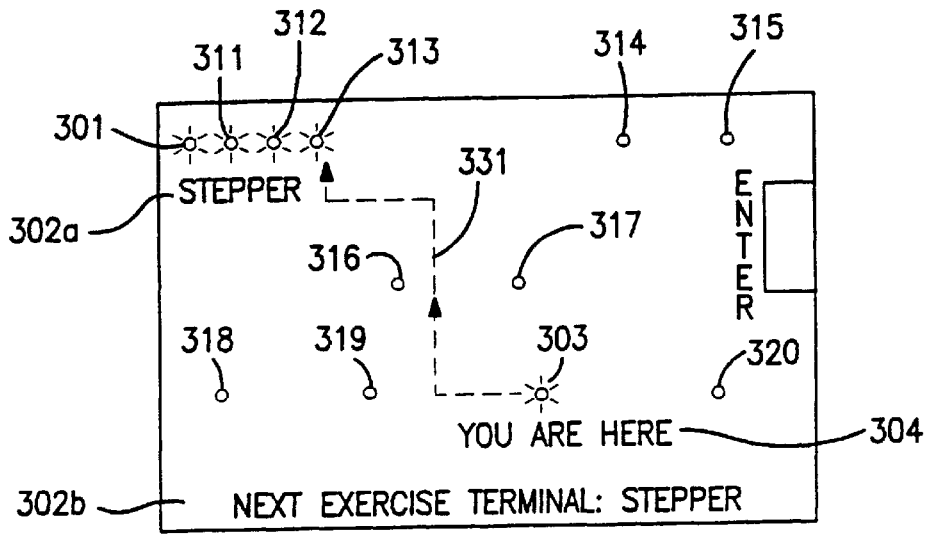
FIGS. 13A and 13B are display screens which may be provided to guide an exerciser using the exercise terminal network 100 of FIG. 3.
Figure 13B:
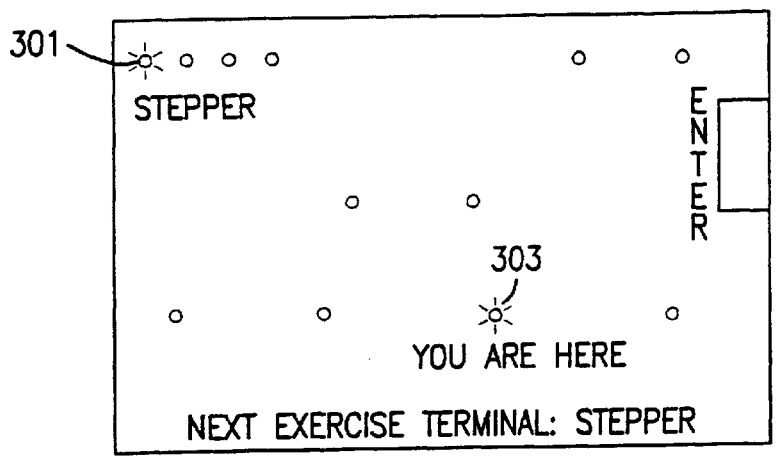

The prompt may also include graphical information as shown in FIGS. 13A and 13B. This prompt including graphical information may be displayed on the display of the exercise terminal (e.g., display portion 303 of stationary bicycle 200 shown in FIG. 7 or display portion 280 of FIG. 8B). FIG. 13A is a prompt which includes a graphical representation of the exercise terminals at a location such as a health club in which a plurality of indicators (in this case, dots) are provided on the display to identify the arrangement and locations of the exercise terminals at the health club. For example, in FIG. 13A, indicators 301, 311, 312, and 313 indicate "steppers"; indicator 314 indicates an exercise station terminal for performing sit-ups; indicator 315 indicates an exercise station for pull-ups; indicators 316 and 317 indicate treadmills; and indicators 303, 318, 319, and 320 indicate stationary bicycles. The display also indicates an entrance to the workout facility to provide an indication to the exerciser of the location of the next terminal to be used relative to a "fixed" feature of the facility. While an entrance is utilized as such a "fixed" feature in FIG. 13A, other features such as a window or a pool may be utilized. In FIG. 13A, the indicators indicating steppers (i.e., indicators 301, 311, 312, and 313) are visually distinguished from the other indicators in order to indicate to the exerciser that the next exercise terminal to be used is a stepper. The indicators may be distinguished by color, brightness, blinking, etc. A first textual identification portion 302a of the next terminal to be used may be provided adjacent to the visually distinguished indicators 301, 311, 312, and 313 and a second textual identification portion 302b of the next terminal to be used may be provided at the bottom portion of the display. The display of FIG. 13A also provides the exerciser with an indication of the location of the exercise terminal currently being used. Specifically, indicator 303 is visually distinguished from the other indicators (by brightness, color, blinking, etc.) and a textual indication 304,(such as "YOU ARE HERE") is provided adjacent to indicator 303. In this way, the relative location of the exercise terminal currently being used and the next exercise terminal to be used can be provided to the exerciser. If desired, a path indication 331 may be provided to guide the exerciser to the next terminal. Also, if desired, textual identifications corresponding to each indicator or group of indicators of the same terminal type may be provided, not just the current terminal and the next terminal.

The display of FIG. 13A identifies the stepper as the next exercise terminal to be used and the indicators for all of the steppers in the health club facility are visually distinguished from other indicators. Alternatively, as shown in FIG. 13B, a particular stepper of all the steppers in the health club facility may be identified as the next exercise terminal to be used by the exerciser. The identification of a particular stepper may be made in order to identify a stepper which is not currently being used or is being "reserved" for use by the exerciser who has just finished using the stationary bicycle indicated by indicator 303.

It will be appreciated that although each exercise terminal is indicated by a dot in FIG. 13A, the invention is not limited in this respect. For example, each exercise terminal may be indicated by an icon or some other graphical (including photographical), video, or animated representation. In this case, each exercise terminal type may have a different icon associated therewith. Video, photographic or animated images of the exercise terminals and/or the health club facility may be used to guide the exerciser through his/her workout. As with the textual information, the graphic display may be any graphic display which provides meaningful guidance to the exerciser with regard to the identification of an exercise terminal to be used next by the exerciser and/or the location of an exercise terminal to be used next by the exerciser.

Figure 14A:
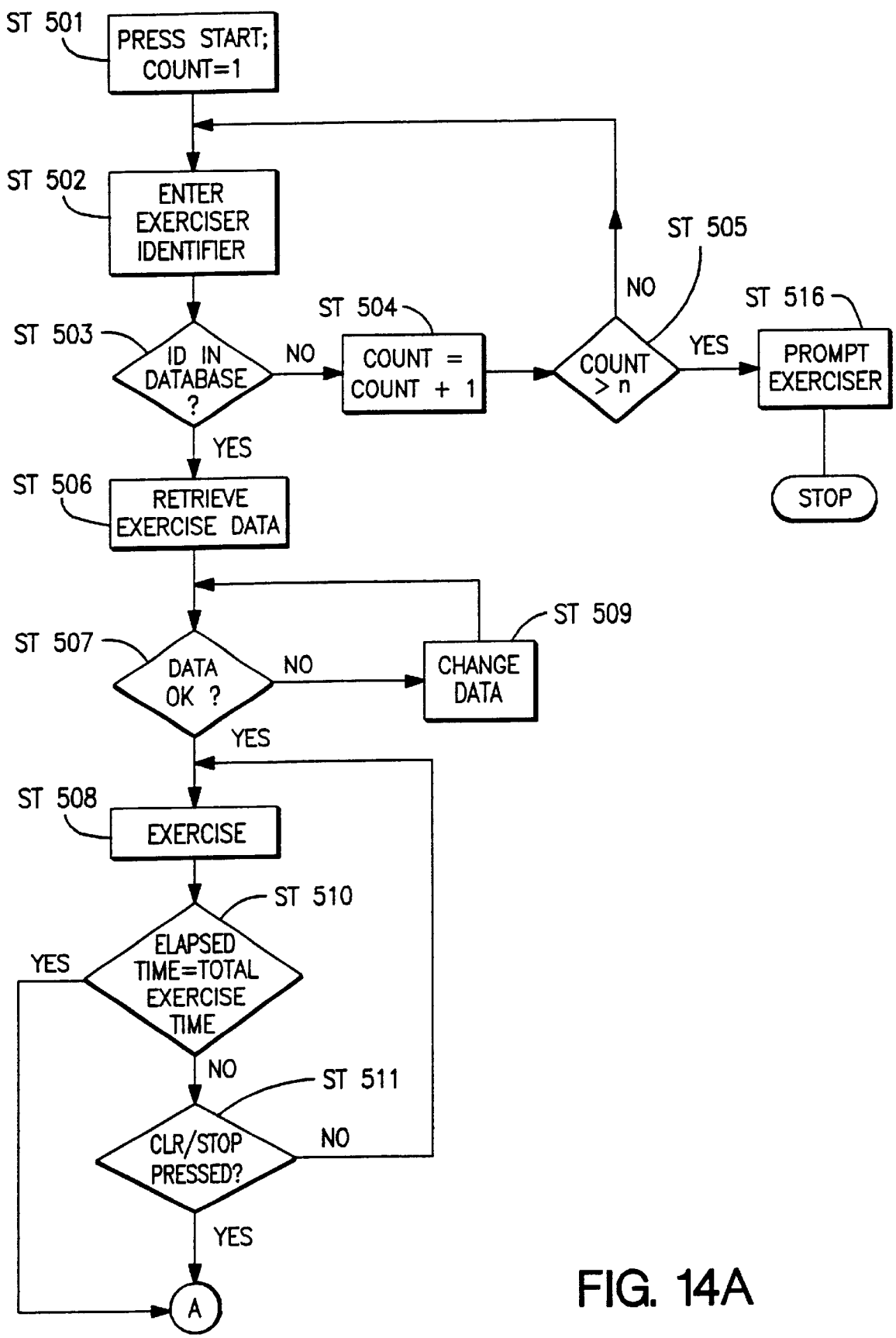
FIGS. 14A–14C are flow charts illustrating operations of exercise terminal network 100.
Figure 14B:
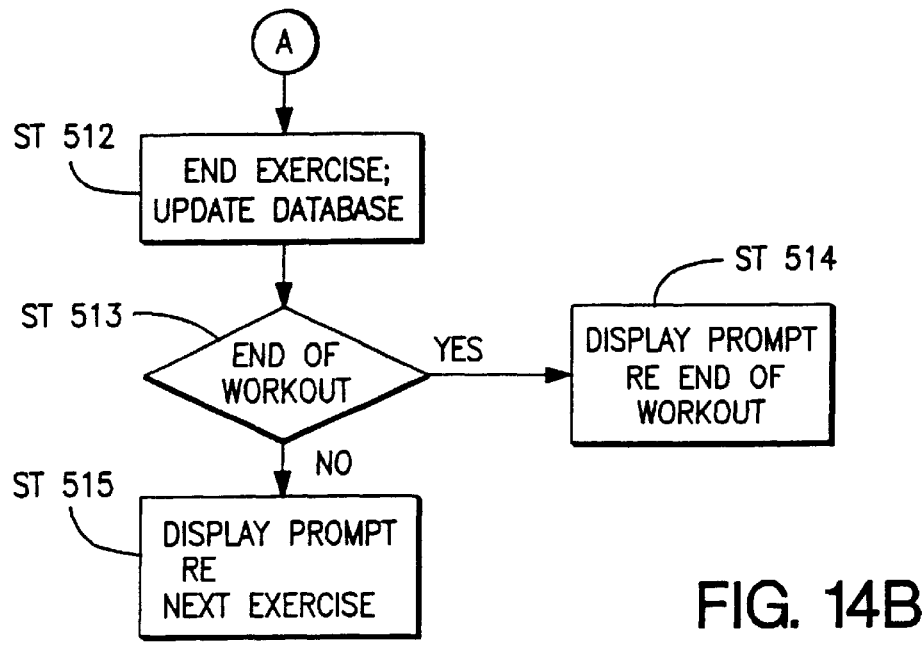

An operation of the exercise terminal network in accordance with the present invention will be described with reference to the flowcharts of FIGS. 14A–14C. It will be assumed for purposes of this discussion that the exercise terminals to be used during the workout have keypads and displays such as those shown FIGS. 7 and 8B. To begin, the exerciser presses START key 332 (ST 501). At this time, a count of a retry counter to be described below is set to one. At ST 502, the exerciser is prompted via a prompt on display portion 280 or 303 to enter an exerciser identifier such as a personal identification number (PIN). The entered exerciser identifier is utilized to access the exercise database. As described above, each exerciser using exercise terminal network 100 is preferably assigned a unique exerciser identifier. In a health club setting, unique exerciser identifiers may, for example, be assigned to each exerciser by the health club operator. If the exerciser identifier is a PIN, is the exerciser may enter the exerciser identifier using the numeric keys 0–9 on numeric keypad portion 293 or 330. In alternative embodiments, exercise terminals in the network may be provided with a bar code reader and the exercisers may be provided with exerciser identification cards which include a bar coded exerciser identifier. The exerciser may, for example, swipe the identification card through the bar code reader to enter his/her exerciser identifier. Of course, other types of identification cards such as magnetic, optical, or semiconductor memory cards may be, used in combination with appropriate readers operatively connected to the exercise terminal and the invention is not limited in this respect.

The processor of the exercise terminal accesses the exercise database to determine whether the entered exerciser identifier is in the exercise database at ST 503. If the entered exerciser identifier is not in the exercise database, control passes to ST 504 and ST 505, where the exerciser is prompted via a prompt on display portion 280 or 303 to re-enter the exerciser identifier. A counter is incremented at ST 504 each time the exerciser enters an exerciser identifier which is not found in the exercise database at ST 503. If the count of the counter is greater than a predetermined retry number n (such as three) at ST 505, the exerciser is prompted via the display portion and/or the speaker(s) at ST 516 that the entered exerciser identifier is not valid and that the system administrator should be contacted.

At ST 503, if the exerciser identifier is in the exercise database, control passes to ST 506 and exercise data is retrieved from the exercise database based on the entered exerciser identifier and the exercise terminal currently being used. Specifically, the processor of the exercise terminal uses the entered exerciser identifier and the exercise terminal identifier to access the exercise database to retrieve the appropriate exercise data For example, in the case of an exercise apparatus terminal such as stationary bicycle 200, the retrieved exercise data includes an exercise identifier identifying an exercise program executable by the processor of the exercise apparatus terminal for varying the exercise level of the stationary bicycle as a function of time and any corresponding exercise parameters (for example, a total exercise time and/or a difficulty level). The retrieved exercise identifier is used by the processor of the exercise apparatus terminal to access one of the exercise programs stored in the ROM of the exercise apparatus terminal, for example. As noted above, the present invention is not limited to the selection of exercise programs stored in the ROM of the exercise apparatus terminal and exercise programs stored in the memory of central computer 102 and/or in a portable memory module may also be accessed. The display of the exercise apparatus terminal displays to the exerciser information regarding the exercise program such as the program name and/or a graphical display of exercise level versus time similar to that of FIG. 6, as well as any corresponding exercise parameters. In the case of an exercise station terminal, the retrieved exercise data may include an exercise identifier, identifying an exercise such as stretching; sit-ups, pull-ups, and the like, and any associated exercise parameters (for example, a number of repetitions and/or a total exercise time). The display of the exercise station terminal displays a text string identifying the exercise (e.g., "stretching", "pull-ups", etc.) and the number of repetitions and/or total exercise time.

The exerciser may use these displays of the exercise terminals to verify the exercise data prior to beginning the exercise. Of course, other data may be displayed and the invention is not limited in this respect. If the exercise data is acceptable to the exerciser at ST 507, the exerciser presses START key 332 to begin exercise ST 508. The exerciser may, if desired, change any of the retrieved exercise data at ST 509.

During exercise, the processor of the exercise terminal controls the display to display relevant exercise data. In the case of an exercise apparatus terminal, such exercise data may include the elapsed exercise time, current difficulty level, desired activity level, actual activity level, and the like. An appropriately illuminated display of exercise level versus time to indicate an exerciser's progress through the exercise program may also be provided. If a pulse monitor is used, the display may also provide either a readout of the exerciser's pulse, or a graphical display indicating whether the exerciser's pulse is in an appropriate target range for the exerciser. In the case of an exercise station terminal for stretching, the display may provide an indication of exercise time elapsed, exercise time remaining, and/or some graphical indication of the progress of the exerciser.

The processor of the exercise terminal may monitor the exerciser's pulse rate during exercise using a pulse monitor. For example, the processor of the exercise terminal may monitor the exerciser's pulse rate at regular predetermined intervals or at predetermined times during exercise. The monitoring of the exerciser's pulse rate permits a determination of whether the exerciser's pulse rate is generally within a range appropriate for achieving the exerciser's goals (e.g., cardiovascular fitness or fat loss). At the end of the exercise when the elapsed time equals the total exercise time (ST 510) or if the CLEAR/STOP key 340 is pressed (ST 511), the processor of the exercise terminal drives the display and/or speaker(s) to output a prompt indicating the end of the program at ST 512 (see FIG. 14B). The processor of the exercise terminal then causes the exercise database to be updated to include an indication that the exercise was completed by the exerciser. The exercise database may also be updated to indicate whether the exerciser changed the pre-selected exercise data and, if so, the exercise data (e.g., exercise program, the total exercise time, and/or difficulty level) which was changed. The exercise database may also be updated to include data regarding the exerciser's pulse rate during exercise. This pulse rate data may be the exerciser's actual pulse rate at various points during the exercise or some average pulse rate over exercise time of the exercise. Further, the system may also store data regarding whether the exerciser changed the exercise parameters of an exercise apparatus terminal during exercise. The exercise terminal may also prompt the exerciser to enter an indication of whether the exerciser felt the exercise was too hard, too easy, or about right. The stopping of exercise prior to completion may also be recorded in the exercise database. It will be appreciated that not all of the above data needs to be stored and that this or other data may be stored for use by the control program and/or the fitness consultant in the pre-selection of exercise data.

At ST 513, a determination is made whether the current exercise is the last exercise in the current workout. If so, a prompt is provided to the exerciser at ST 514 indicating that the workout is over. If not, a prompt is provided to the exerciser at ST 515 indicating which exercise terminal should be utilized next by the exerciser. Such a prompt was discussed above with respect to FIGS. 13A and 13B and the accompanying description.

Figure 14C:
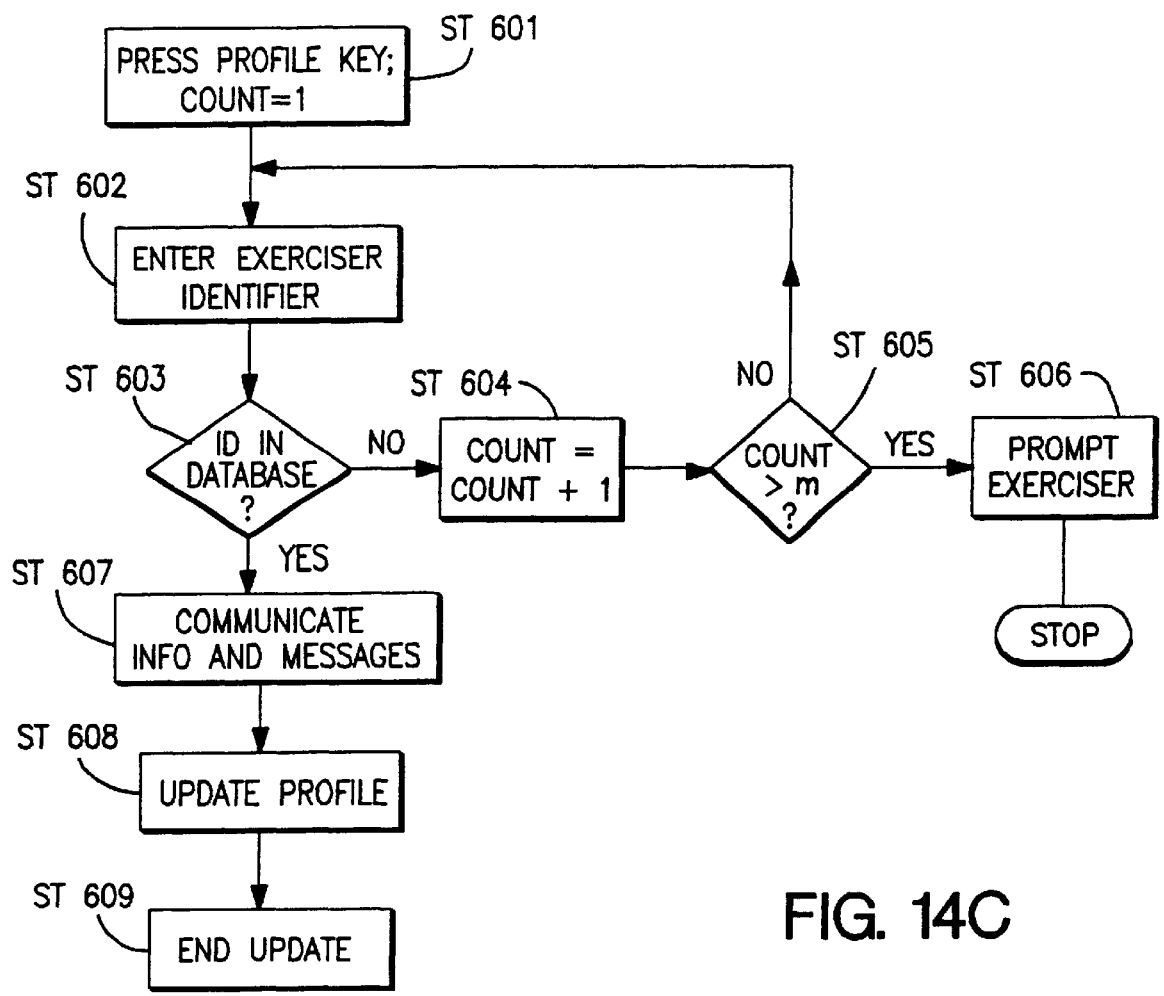

FIG. 14C is a flow chart illustrating a process for updating the exercise database. The updating may be performed periodically. For example, the exerciser may be prompted to perform such an update after the last exercise of a workout. The updating of the exercise database may be accomplished using an input device and display device associated with the central computer or using a computer connected to the central computer. The updating can also be performed using an input device(s) and display(s) of an exercise apparatus terminal or an exercise station terminal. In the case of an exercise terminal, the updating process may be started at ST 601 by pressing PROFILE key 342 on keypad 207. At this time, the count of a retry counter is reset to one. Similarly, a predetermined key sequence or a menu selection may be utilized to start the updating process using the central computer or some other computer connected to the central computer. At ST 602, the exerciser inputs an exerciser identifier using the input device which may be a keypad or a bar code reader, for example. The exercise database is accessed to determine whether the entered exerciser identifier is in the exercise database at ST 603. If the entered exercise identifier is not in the exercise database, control passes to ST 604 and ST 605 where the exerciser is prompted via a prompt on the display device of the central computer, a display device of the computer connected to the central computer, or the display device of the exercise terminal to re-enter the exerciser identifier. A counter is incremented at ST 604 each time the exerciser enters an exerciser identifier which is not found in the exercise database at ST 603. If the count of the counter is greater than a predetermined retry number m (such as three) at ST 605, the exerciser is prompted via the appropriate display and/or speaker(s) at ST 606 that the entered exerciser identifier is invalid and that the system administrator should be contacted. If the exerciser identifier is found in the exercise database at ST 603, information and messages may be communicated to the exerciser visually and/or aurally at ST 607. The information may, for example, inform the exerciser about upcoming health club matters such as closings, changed hours, etc. or about upcoming health club events. Messages to the exerciser from the system administrator or a fitness consultant may also be reviewed at this time. When the exerciser is finished reviewing any information or messages at ST 607, the exerciser may be prompted for various inputs, for example, to update the exerciser profile at ST 608. The exerciser may be prompted to input, for example, his/her current weight; to update any exercise goals such as a race in which the exerciser will participate; etc. It will be appreciated that various interfaces for updating profile data may be utilized and the invention is not limited in this respect. When the exerciser's input is complete, the process ends at ST 609. This updating may even take place while an exerciser is exercising using prompts displayed on the display of an exercise apparatus terminal or exercise station terminal.

Various factors which may be utilized in the selection of exercises and workouts by the system control program and/or a fitness consultant will now be described. In a first instance, suppose the exerciser had entered an exerciser profile indicating a fitness goal of fat loss. If the pulse rate of the exerciser as monitored by the processor of an exercise terminal during the exercises of previous workouts is generally outside the range for fat loss, for example, below 65% of the exerciser's maximum heart rate, the system control program or the fitness consultant may subsequently select exercises which are "harder" in order to increase the exerciser's pulse rate up into the range which is best suited to achieve fat loss, i.e., between about 65% and 75% of the exerciser's maximum heart rate. Similarly, if the pulse rate of the exerciser as monitored by the processor of an exercise terminal during the exercises of previous workouts is generally too high for achieving fat loss, i.e., above 75% of the exerciser's maximum heart rate, the system control program or the fitness consultant may subsequently select exercises which are "easier" in order to decrease the exerciser's pulse rate down into the range which is best suited to achieve fat loss, i.e., between about 65% and 75% of the exerciser's maximum heart rate. As an exerciser continues a training routine, it will be likely that harder exercises will need to be selected to ensure that an exerciser's pulse rate is within the range best suited for achieving fat loss so that the full benefits of workouts may be obtained.

In a second instance, the system control program or the fitness consultant may base the exercise selection on a particular fitness goal of the exerciser, e.g., playing soccer, playing tennis, playing golf playing basketball, playing hockey, playing baseball, skiing, etc. Such a fitness goal may be entered in the exerciser's profile and then utilized by the system control program or the fitness consultant in the selection, over time, of a sequence of exercises and workouts designed to train the exerciser for the selected fitness goal. For example, for an exerciser who plays tennis, the system control program or the fitness consultant may select exercises and workouts which are best suited for getting an exerciser in "tennis shape", e.g., exercises which have alternating relatively short periods of high exercise levels (corresponding to volleys) and relatively short periods of low exercise levels (corresponding to the time between points). Similarly, for an exerciser who plays soccer, the system control program or fitness consultant may select exercises and workouts which are best suited for getting an exerciser in "soccer shape", e.g, exercises which have relatively long periods of moderate exercise levels and relatively short periods of high activity levels. In addition, the system control program or fitness consultant may also, base the selection for complementing the training of an exerciser for some event, for example, running a five kilometer race, running a ten kilometer race, running a marathon, bicycling in a bicycle race of some distance, etc. The event may even be more specifically defined, e.g., running a ten kilometer race on a particular date in the future. Taking into account the current date, the system control program or fitness consultant may select a sequence of exercises and workouts designed to complement other training of the exerciser (e.g., road work) for the race on the particular day. The information as to the exerciser's fitness goals may also permit the system control program or the fitness consultant to select exercises which "balance" utilization of various muscle groups. For instance, if an exerciser selects a goal associated with running, the system control program or fitness consultant may select exercises which attempt to compensate for the greater use of certain muscles during running. Of course, the system control program or fitness consultant may base the exercise selection on a combination of the first and second instances, i.e., a combination of a particular fitness goal such as running, basketball, etc. and an indication of whether fat loss or cardiorespiratory fitness is desired.

In a third instance, the system control program or fitness consultant may base the exercise selection on pulse rates determined by a physician for a rehabilitation program of a patient. For example, the physician may determine that the patient's pulse rate during exercise should be in range defined by a first, lower pulse rate and a second, higher pulse rate. Thus, if the processor of an exercise terminal monitors that the patient's pulse rate was generally below the first pulse rate during one or more previous exercises or workouts, the system control program or the fitness consultant may subsequently automatically select harder exercises and workouts. Similarly, if the patient's pulse rate generally exceeded the second pulse rate during one or more previous exercises or workouts, the system control program or the fitness consultant may subsequently select easier exercises. In situations where a patient's pulse rate must be carefully controlled, the system control program may include a routine for automatically changing the difficulty level and/or exercise time during exercise if the patient's pulse rate is too high or too low. Such changes may be stored in the exercise database and utilized by the system control program or fitness consultant in the subsequent selection of exercises and workouts.

In a fourth instance, the system control program or fitness consultant may base the exercise selection on a current date. For example, persons are more likely to gain weight during the year-end holidays. Accordingly, the system control program or fitness consultant may select exercises which are designed to achieve fat loss during this time of the year. In addition, during winter months, e.g., December, January, and February, an exerciser's outdoor activities may be reduced. Accordingly, the system control program or the fitness consultant may select exercises of increased exercise time and/or difficulty in order to compensate for the reduced outdoor activities in order to better maintain the exerciser's fitness level.

The system control program of central computer 102 may include additional routines for implementing various other features of the present invention. For example, the system control program may include a routine for permitting the periodic and/or automatic tracking of the progress of one or more the exercisers. Such a routine may periodically scan the exercise database to determine, for example, if there are any exercisers who have missed one or more workouts, who have not worked out for some period of time, or whose physiological data collected during exercise indicates inadequate progress. The routine of the system control program may then output data on a display screen or on printing device which identifies such exercisers so that the administrator of the central computer can notify the appropriate fitness consultants. In an alternative implementation, the routine of the control program may output and forward an e-mail (electronic mail) message to the fitness consultant. In either case, the fitness consultant can quickly be made aware of possible problems in the exerciser's work habits or, of some illness or injury preventing the exerciser from working out. This feedback of the exerciser's activities permits a more hands-on approach to be taken by the fitness consultant. In still another alternative embodiment, the routine of the control program may output and forward an e-mail message to the exerciser.

The control program of central computer 102 may also include a routine which monitors which exercise terminals are currently being used by exercisers. Such a routine is particularly useful in a health club setting, although its implementation is not limited in this respect. By monitoring which exercise terminals are currently in use, the routine can verify that an exercise terminal of the type to be used next by an exerciser is available. In this way, the display of FIG. 13B which indicates a specific exercise terminal to be used next may be generated. If an exercise terminal of the type to be used next is not available, the system control program can select an exercise terminal which is available. For example, if the next exercise terminal to be used by an exerciser in a preselected workout is a stepper, but all the steppers are currently being used, the system control program can direct the exerciser to a stationary bicycle. If appropriate, after using the stationary bicycle, the exerciser may be directed to the stepper. In this way, the exerciser is not kept waiting to use exerciser terminals.

Figure 15A:
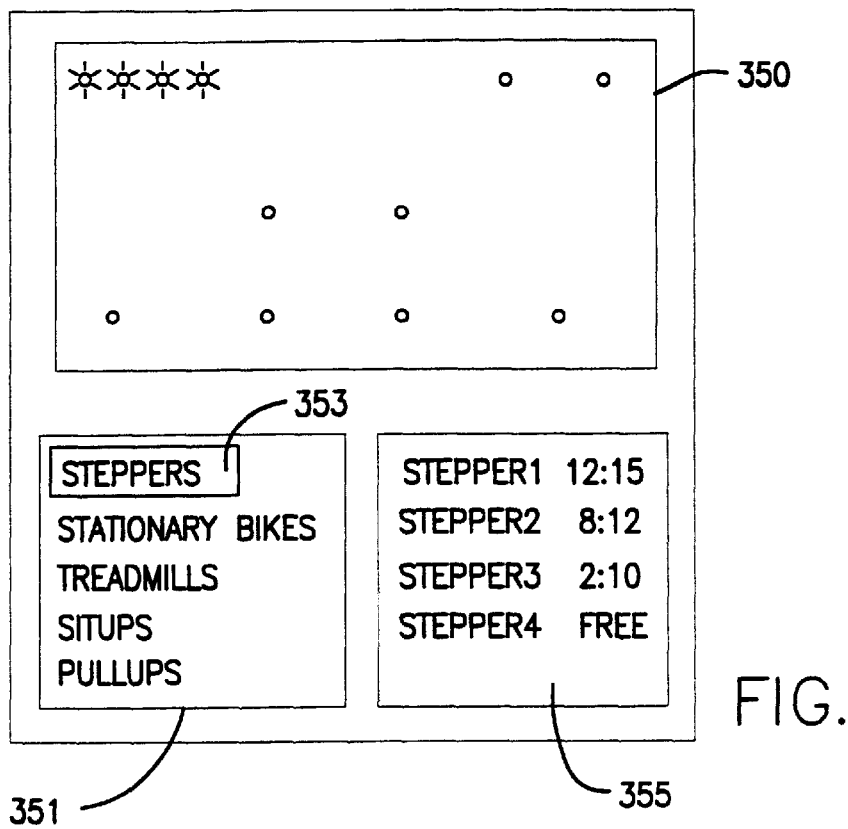
FIGS. 15A–15E are display screens for communicating to an exerciser which exercise terminals are currently in use and for providing a terminal reservation capability.
Figure 15C:
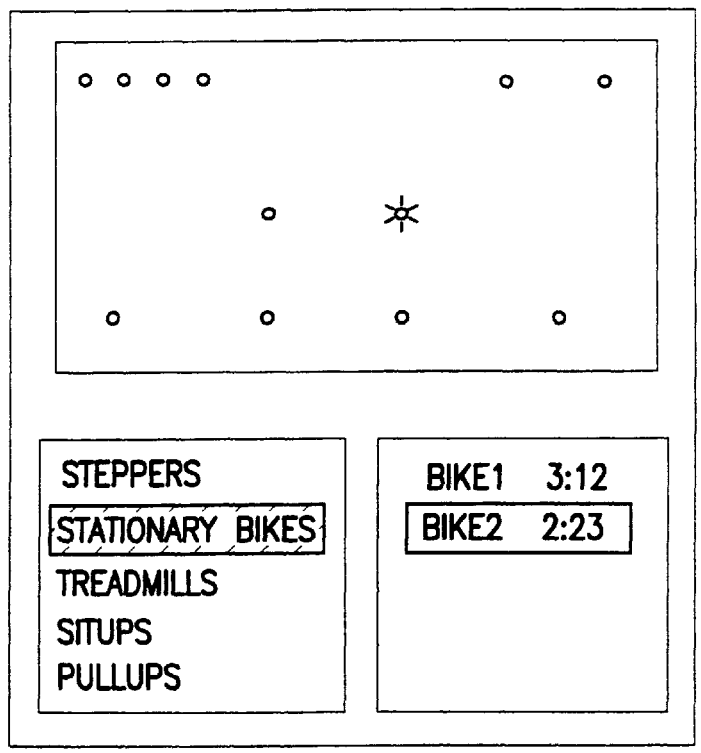
Figure 15B:
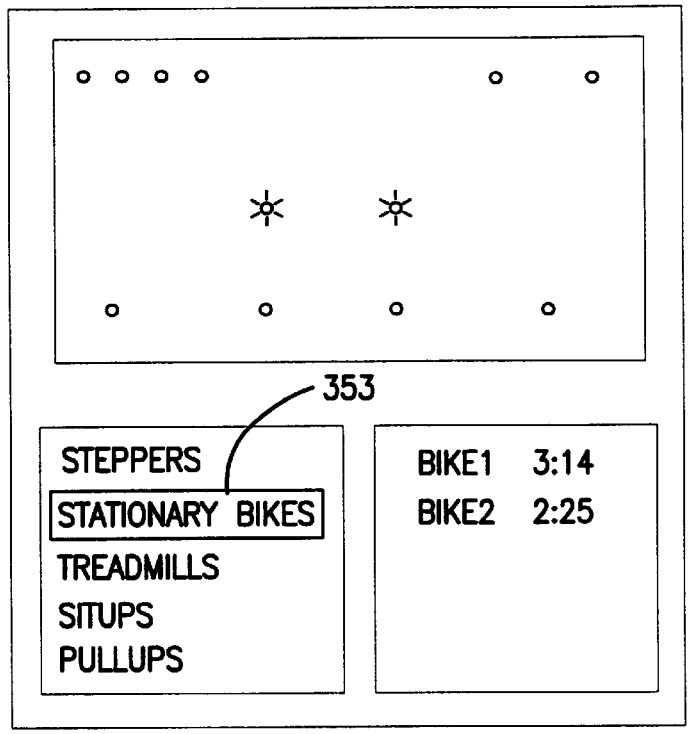

In addition, a routine for monitoring which exercise terminals are currently being used may be used to inform exercisers which exercise terminals are currently available and how much time remains in the exercises for exercise terminals which are currently being used. This routine is particularly useful at peak use times of a health club and permits exercisers to determine when certain exercise terminals may be free. The exercisers may access this information using a display and a keyboard and/or pointing device (such as a mouse) of central computer 102. An example of a screen which may be presented on the display of central computer 102 to inform exercisers is shown in FIG. 15A. The upper portion 350 of the display is similar to the displays of FIGS. 13A and 13B and shows the arrangement and locations of the exercise terminals at the health club. The list box 351 lists the types of exercise terminals at the health club, i.e., steppers, stationary bicycles, treadmills, sit-up station, and pull-up station. A cursor 353 may be positioned to highlight one of the terminal types in this list using the keyboard or the pointing device. The indicators in the upper display portion 350 which correspond to the highlighted terminal type are visually distinguished from other indicators. In this case, the cursor 353 is positioned on the list choice "STEPPERS" and thus indicators 301, 311, 312, and 313 are visually distinguished from other indicators. The list box 355 lists each terminal in the health club of the type highlighted in list box 351. Thus, in this case, list box 355 lists the four steppers corresponding to indicators 301, 311, 312, and 313 of the upper display portion 350. For each stepper, an indication is provided as to whether that stepper is free (i.e., not currently being used) or as to how much time remains in the current exercise program which is being executed. As shown in FIG. 15A, stepper 1 has 12:15 (12 minutes, 15 seconds) remaining in the current exercise program; stepper 2 has 8:12; stepper 3 has 2:12; and stepper 4 is free. In FIG. 15B, the cursor has been positioned to highlight "STATIONARY BICYCLES" in list box 351. Thus, indicators 316 and 317 are visually distinguished from other indicators and list box 355 lists the stationary bicycles corresponding to indicators 316 and 317. As shown in FIG. 15B, stationary bicycle 1 has 3:14 remaining in the current exercise program and stationary bicycle 2 has 2:25 remaining. As shown in FIG. 15C, the cursor may be positioned in the list box 355 and positioned to highlight one of the stationary bicycles, e.g., stationary bicycle 2. In this case, only indicator 317 corresponding to stationary bicycle 2 is visually distinguished from other indicators.

Figure 15D:
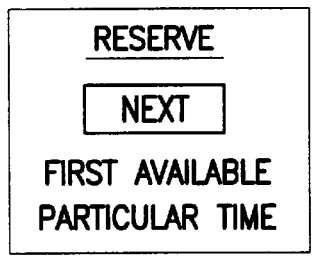
Figure 15E:
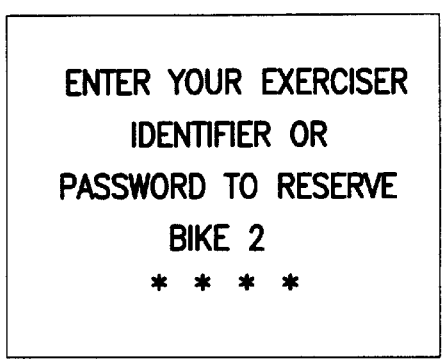

The system control program may also include a routine which permits exercisers to reserve particular exercise terminals using, for example, their exerciser identifiers. The reservation may be for a particular time, e.g., 6:30 p.m.; for a particular terminal when it becomes free; or for any terminal of a particular type when it becomes free. The exerciser may then begin exercising on another terminal. When the reserved terminal becomes free, the exerciser is provided with a prompt at the terminal at which he/she is currently exercising. The prompt may be either visual (e.g., on the display of the exercise terminal) or aural (using the speaker of the exercise terminal). The exerciser may then confirm his/her intention to use the reserved exercise terminal or may cancel the reservation to free the exercise terminal. If the exerciser confirms his/her intention to use the reserved exercise terminal the reserved terminal is then available only for his/her use for some period of time, e.g., two minutes. During this time, other exercisers will be "locked-out" from using the exercise terminal. Specifically, the exercise terminal can be used only by entering, the exerciser identifier or some password of the exerciser who reserved the exercise terminal. Alternatively or in addition, the central computer may cause an announcement over a loudspeaker (or loudspeakers) positioned in the health club. Still further, when the reserved terminal becomes free, the exerciser may be paged using a paging system. Such a pager system could, for example, be similar to a pager system used in restaurants. The reservation may be placed using an interface similar to the interface described above with respect to FIGS. 15A–15C. For example, a predetermined keypress from the screen of FIG. 15C may bring up a reservation screen such as the screen of FIG. 15D. As suggested by FIG. 15D, the exerciser may reserve stationary bicycle 2 "NEXT", i.e., at the end of the current exercise program or at a "PARTICULAR TIME". The exerciser is also given the option to reserve the first available stationary bicycle, i.e., whichever one of stationary bicycles 1 and 2 is free first. Selection of these choices leads the exerciser to a screen such as that of FIG. 15E where the exerciser is prompted to enter his/her exerciser identifier or password in order to complete the reservation process. It will be apparent that more sophisticated reservation processes, taking into account, for example, reservations by other exercisers, may be implemented within the spirit of the present invention.

In addition, a display such as the display of FIG. 15A may be provided on the display of an exercise terminal. Such a display may, for example, be automatically generated as an exerciser's current exercise at an exercise terminal is finishing up, e.g., when there is less than a minute left in the current exercise. The exerciser may use NEXT and PREV keys 336 and 338 to position a cursor so as to highlight one of the exercise terminal types in list box 351. The exerciser can use this information in making his/her determination as to which exercise terminal he/she should use next. In another implementation, the exerciser may press a numeric key corresponding to one of the steppers, for example, to reserve that stepper for some predetermined period of time. It is noted that these features for providing information regarding other exercise terminals and for reserving exercise terminals may be implemented independently of the automatic "next exercise terminal" feature described above.

The system control program of central computer 102 may also include a lock-out routine for locking out other exercisers when a first exerciser is finishing up a program (e.g., less than two minutes remaining) on a first exercise terminal and the exercise database includes workout data whereby the first exerciser is to use a second exercise terminal when he/she is finished using the first exercise terminal. Assuming the second exercise terminal is currently available, the lock-out routine of the system control program would not permit other exercisers to begin using the second exercise terminal. For example, when the second exerciser enters his/her exerciser identifier into the second exercise terminal, a prompt may be displayed on the display portion of the exercise terminal indicating the exercise terminal is not currently available to be used. However, when the first exerciser enters his/her exerciser identifier, the lock-out routine does not lock out the first exerciser from using the second exercise terminal.

Central computer 102 may also utilize an e-mail link for communication to/from exercisers. For example, a fitness consultant may advise an exerciser that workout days using the exercise terminal network should be intermixed with workout days of other exercises including, but not limited to, walking, swimming, biking, tennis, golf, or jogging. In one implementation, another routine of the system control program may query an exerciser via e-mail as to whether any such activity was performed on a day when the exerciser does not go to the health club. For example, the routine of the system control program may scan the exerciser database to determine which exercisers did not work out using an exercise terminal connected in the exercise terminal network on a previous day. The routine may then generate and forward:,an e-mail message to these exercisers asking about any activity or activities which they may have performed on that previous day. The e-mail message may, for example, comprise a form-like message having check boxes and edit fields which the exerciser can "fill-in" and return to the central computer as an e-mail reply. The form-like message for a particular exerciser may be a generic message suitable for all the exercisers using the network or may be generated based on activities in which the exerciser indicates to the fitness consultant that he/she participates. The e-mail reply is used by central computer 102 to appropriately update the exercise database. In this way, an accurate record of all activities by the exerciser may be maintained in the exercise database and utilized in selecting appropriate work-outs which use the exercise terminals of the exercise network and which involve other exercise activities.

Yet another routine of the control: program may generate and forward to an exerciser an e-mail message setting forth a workout for the exerciser on a particular day or days. The exerciser may then indicate via a reply e-mail message whether he/she performed the suggested work-out (or some other workout, if any).

Figure 16:
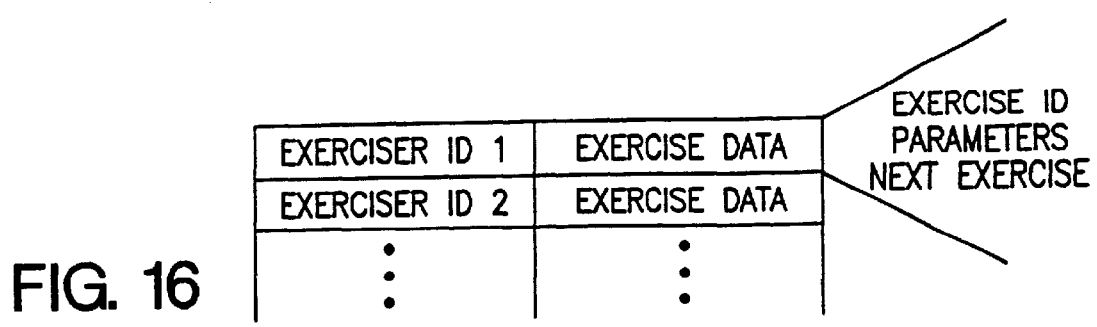
FIG. 16 illustrates a table which is stored in the memory of an exercise apparatus in accordance with a second embodiment of the present invention.

While the invention has been described in terms of terminals connected to a central computer, certain features may be implemented in a stand-alone terminal by providing a table such as the table of FIG. 16 in the memory (e.g, $E^2PROM$) of each exercise terminal. The table of FIG. 16 defines a relationship between exercisers and exercises. Specifically, the table of FIG. 16 includes exerciser identifiers each of which is associated with an exerciser. The exerciser identifiers may, for example, be exerciser identifier numbers. For each exerciser identifier, the table identifies exercise data such as an exercise identifier, exercise parameters (e.g., a total exercise time and a difficulty level), and "next" exercise data. For example, exercise program 1, a total exercise time parameter of 8:00 minutes, a difficulty level parameter of 8, and an exerciser terminal type identifier of 13 may be associated with exerciser identifier 1. It will be appreciated that the total exercise time and/or the difficulty level may be omitted, if desired. The exercise terminal type identifiers may be provided in order to provide a prompt to an exerciser regarding the next exercise terminal to be used by the exerciser. In this regard, when an exercise program is completed, a database portion such as the database portion of FIG. 11B is accessed using the exercise terminal type identifier to generate a prompt for prompting the exerciser as to which exercise terminal type should be utilized next. This prompt may be a visual prompt using a display, an aural prompt using a speaker(s), or a combined visual and aural prompt using both a display and a speaker(s) as described above with respect to FIGS. 13A and 13B. In order to use the stand-alone terminal, the, exerciser enters his/her exerciser identifier and the processor uses the entered exercise identifier to access the table of FIG. 16. From the table, the processor selects a program from memory and sets the appropriate total exercise time and/or difficulty level. The exerciser may, if desired, change these preselected data items. The user may then begin exercise. The memory may also be configured to allocate some memory for storing data such as pulse rate during exercise and/or to store any changes which were made to the program data by the exerciser. The data constituting the table of FIG. 16 may be periodically provided to the ROM of the exercise terminal using, for example, a portable memory module or a computer connected to the exercise terminal using the I/O port.

Each of the above-referenced issued patents and patent applications are hereby incorporated by reference into the instant specification.

While there has been shown and described various embodiments of the present invention, it will be evident to those skilled in the art that various modifications may be made thereto without departing from the scope of the invention which is set forth in the appended claims.

I claim:

1. An exercise system for guiding exercisers from one exercise terminal to another, the exercise system comprising:
   a plurality of exercise terminals each usable for performing a different exercise;
   a system computer connected to the exercise terminals via a communication link;
   the system computer being configured to determine for an exerciser, based on predetermined exerciser data stored in a memory accessible to the system computer, a next exercise terminal at which the exerciser should exercise after ending exercise at a currently-used exercise terminal; and to communicate to the currently-used exercise terminal via the communication link data regarding the next exercise terminal; and
   the currently-used exercise terminal comprising an output device for outputting to the exerciser data that directs the exerciser to exercise at the next exercise terminal.

2. The exercise system according to claim 1, wherein the currently-used exercise terminal comprises monitoring means for monitoring the exerciser while the exerciser exercises and the system computer determines whether to vary the next exercise terminal from that specified by the predetermined exerciser data based on the monitoring.

3. The exercise system according to claim 2, wherein the monitoring means monitors physiological parameters of the exerciser.

4. The exercise system according to claim 2, wherein the monitoring means monitors the exerciser by detecting whether the exercise at the current exercise terminal is ended prematurely.

5. The exercise system according to claim 2, wherein the monitoring means monitors the exerciser by detecting whether the exerciser changes a difficulty level of the exercise at the current exercise terminal.

6. The exercise system according to claim 2, wherein the monitoring means monitors the exerciser by detecting an input of the exerciser's perception of a difficulty of the exercise at the current exercise terminal.

7. An exercise system for guiding exercisers from one exercise terminal to another, the exercise system comprising:
   a plurality of exercise terminals each usable for performing a different exercise;
   a system computer connected to the exercise terminals via a communication link;
   the system computer being configured to evaluate one or more factors during the workout of the exerciser; to determine for the exerciser, based at least in part on the evaluation of the factors, a next exercise terminal at which the exerciser should exercise after ending exercise at a currently-used exercise terminal; and to communicate to the currently-used exercise terminal via the communication link data regarding the next exercise terminal; and
   the currently used exercise terminal comprising an output device for outputting to the exerciser data that directs the exerciser to exercise at the next exercise terminal.

8. The exercise system according to claim 7, wherein the performance of the exerciser during one or more exercises constitutes one of the one or more factors.

9. The exercise system according to claim 8, wherein the performance of the exerciser is based on a monitoring of physiological parameters of the exerciser.

10. The exercise system according to claim 7, wherein the use/non-use states of the exercise terminals constitutes one of the one or more factors.

11. The exercise system according to claim 7, wherein an indication by the exerciser as to certain physical limitations constitutes one of the one or more factors.

12. The exercise system according to claim 7, wherein a time limitation of the exerciser for completing the workout constitutes one of the one or more factors.

13. The exercise system according to claim 7, wherein the burning of a predetermined number of calories by the exerciser constitutes one of the one or more factors.

14. An exercise system for guiding exercisers from one exercise terminal to another, the exercise system comprising:
   a plurality of exercise terminals each usable for performing a different exercise; and
   a system computer connected via a communication link to the exercise terminals, the system computer determining a next exercise terminal at which an exerciser should exercise after ending exercise at a currently-used exercise terminal, and communicating to the currently-used exercise terminal data regarding the next exercise terminal, wherein
      the currently-used exercise terminal comprises an output device which outputs to the exerciser data that directs the exerciser to exercise at the next exercise terminal.

15. The exercise system according to claim 14, wherein the currently-used exercise terminal comprises monitoring means for monitoring the exerciser while the exerciser exercises and the system computer determines the next exercise terminal based on the monitoring.

16. The exercise system according to claim 15, wherein the monitoring means monitors physiological parameters of the exerciser.

17. The exercise system according to claim 15, wherein the monitoring means monitors the exerciser by detecting whether the exercise at the currently-used exercise terminal is ended prematurely.

18. The exercise system according to claim 15, wherein the monitoring means monitors the exerciser by detecting whether the exerciser changes a difficulty level of the exercise at the currently-used exercise terminal.

19. The exercise system according to claim 15, wherein the monitoring means monitors the exerciser by detecting an input of the exerciser's perception of difficulty of the exercise at the currently-used exercise terminal.

20. The system according to claim 15, wherein, based on the monitoring, the system computer determines parameters of the exercise at the next exercise terminal.

21. The system according to claim 16, wherein the next exercise terminal is a processor-controlled exercise apparatus and the parameters of the exercise include designations of one or more of an exercise program for execution by the processor, an exercise difficulty level and an exercise time.

22. The exercise system according to claim 14, further comprising a computer-readable medium accessible to the system computer for storing predetermined exerciser data for the exerciser, and
   wherein the system computer determines the next exercise terminal based on the predetermined exerciser data stored in the memory.

23. The exercise system according to claim 22, wherein the currently-used exercise terminal comprises monitoring means for monitoring the exerciser while the exerciser exercises and the system computer varies the next exercise terminal from that specified by the predetermined exerciser data based on the monitoring.

24. The exercise system according to claim 14, wherein the system computer further determines if the exerciser's workout is over and, if so, communicates to the currently-used exercise terminal end-of-workout data, and
   wherein the output device of the currently-used exercise terminal outputs to the exerciser the end-of-workout data.

25. The exercise system according to claim 14, wherein the communication link comprises a wireless communication link.

26. The exercise system according to claim 14, wherein the communication link comprises a wired communication link.

27. The exercise system according to claim 14, wherein the data indicative of the next exercise terminal comprises location data indicative of the physical location of the next exercise terminal.

28. The exercise system according to claim 14, wherein the data indicative of the next exercise terminal comprises location data indicative of the physical location of the next exercise terminal relative to the physical location of the currently-used exercise terminal.

29. The exercise system according to claim 14, wherein the data indicative of the next exercise terminal comprises location data for graphically indicating the physical location of the next exercise terminal.

30. The exercise system according to claim 14, wherein the exercise terminals comprise a stationary bicycle.

31. The exercise system according to claim 14, wherein the exercise terminals comprise a treadmill.

32. The exercise system according to claim 14, wherein the exercise terminals comprise a stepper.

33. The exercise system according to claim 14, wherein the exercise terminals comprise a weight machine.

34. The exercise system according to claim 14, wherein the exercise terminals are located at a health club facility.

35. The exercise system according to claim 14, wherein the system computer determines the next exercise terminal based, at least in part, on the use/non-use states of the exercise terminals.

36. The exercise system according to claim 14, wherein the system computer determines the next exercise terminal based, at least in part, on an indication by the exerciser as to certain physical limitations.

37. The exercise system according to claim 14, wherein the system computer determines the next exercise terminal based, at least in part, on an exerciser time limitation for completing a workout.

38. The exercise system according to claim 14, wherein the system computer determines the next exercise terminal based, at least in part, on the burning by the exerciser of a predetermined number of calories.

39. The exercise system according to claim 14, wherein the output device comprises a display device.

40. The exercise system according to claim 14, wherein the output device comprises a speaker.

41. An exercise system for guiding exercisers from one exercise terminal to another, the exercise system comprising:
   a plurality of exercise terminals each usable for performing a different exercise; and
   a processing system which determines a next exercise terminal at which an exerciser should exercise after ending exercise at a currently-used exercise terminal,
   wherein the currently-used exercise terminal comprises an output device which outputs to the exerciser data indicative of the next exercise terminal in order to direct the exerciser to exercise at the next exercise terminal, and
   wherein the next exercise terminal determined for a first exerciser using the currently-used exercise terminal is different than the next exercise terminal determined for a subsequent, second exerciser using the same exercise terminal.

* * * * *